United States Patent [19]
Woodcock et al.

[11] Patent Number: 5,929,039
[45] Date of Patent: Jul. 27, 1999

[54] METHOD FOR TREATING CARDIAC DYSFUNCTION AND PHARMACEUTICAL COMPOSITIONS USEFUL THEREFOR

[75] Inventors: Elizabeth Anne Woodcock, Middle Park; Karen Elizabeth Anderson, Brighton; Anthony Michael Dart, East Malvern; Xiao-Jun Du, Windsor, all of Australia

[73] Assignee: Baker Medical Research Institute, Prahran, Australia

[21] Appl. No.: 08/646,362

[22] PCT Filed: Nov. 15, 1994

[86] PCT No.: PCT/AU94/00702

§ 371 Date: Aug. 5, 1996

§ 102(e) Date: Aug. 5, 1996

[87] PCT Pub. No.: WO95/13818

PCT Pub. Date: May 26, 1995

[30] Foreign Application Priority Data

Nov. 15, 1993 [AU] Australia ............................. PM2423/93

[51] Int. Cl.[6] ............................ A61K 31/13; A61K 31/70
[52] U.S. Cl. ................................. 514/37; 514/39; 514/40; 514/41; 514/674
[58] Field of Search .................................. 514/40, 39, 41, 514/674

[56] References Cited

FOREIGN PATENT DOCUMENTS

WO8804925  7/1988  WIPO .
WO8900848  2/1989  WIPO .
WO900061   1/1990  WIPO .

OTHER PUBLICATIONS

Casti et al. (1975) "Changes in specific radioactivity and levels of free nucleotides and polyamines in infarcted and borderline tissue of reperfused dog heart" *Chemical Abstracts 83*: 364, 16179n.

Natanson et al, Am. J. Physiol, 259(5, Pt. 2) (Abstract), 1990.

Voorn et al, J. Infect. Dis., 163(3) 640–3 (Abstract), 1991.

Ramos et al, Antimicrob. Agents Chem Other 36(9) 1864–9 (Abstract), 1992.

*Primary Examiner*—Leonard Schenkman
*Attorney, Agent, or Firm*—Baker & Botts, LLP

[57] ABSTRACT

The present invention relates generally to a method for, and pharmaceutical compositions useful in, the prophylaxis and/or treatment of cardiac dysfunction in a mammal by the administration of an effective amount of an agent capable of blocking or inhibiting the effect or release of inositol(1,4,5)trisphosphate in cardiac tissue.

31 Claims, 12 Drawing Sheets

METHOD FOR TREATING CARDIAC DYSFUNCTION AND PHARMACEUTICAL COMPOSITIONS USEFUL THEREFOR

This application is a 371 of PCT/Au94/00702 filed Nov. 15, 1994.

The present invention relates generally to a method for, and pharmaceutical compositions useful in, the prophylaxis and/or treatment of cardiac dysfunction in a mammal by the administration of an effective amount of an agent capable of blocking or inhibiting the effect or release of inositol(1,4,5)trisphosphate in cardiac tissue.

Bibliographic details of the publications numerically referred to in this specification are collected at the end of the description.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

The phosphatidylinositol (PtdIns) turnover pathway is a complex signal transduction system that mediates a diverse range of neurotransmitter and hormone induced responses in a great variety of cells (1). The pathway usually involves the receptor mediated hydrolysis of a membrane phospholipid phosphatidylinositol(4,5)bisphosphate (PtdIns(4,5)P$_2$) by a specific phospholipase C (PLC) causing the release of two well described second messengers sn-1,2-diacylglycerol (DAG) and inositol(1,4,5)trisphosphate, hereinafter denoted as Ins(1,4,5)P$_3$. DAG activates protein kinase C (PKC) and Ins(1,4,5)P$_3$ releases calcium from specific intracellular stores. The two arms of the pathway either separately or in concert, control a wide range of cellular responses including contraction, secretion and mitogenesis (2). Ins(1,4,5)P$_3$ is metabolised rapidly within the cell by dephosphorylation via Ins(1,4)P$_2$ to Ins(4)P$_1$ and by phosphorylation to Ins(1,3,4,5)P$_4$, which is further metabolised to produce a wide range of inositol phosphate isomers (FIG. 1). Ins(1,3,4,5)P$_4$ itself has been suggested to have a role in calcium sequestration (3) and roles for other inositol phosphates have been suggested (4).

The PtdIns pathway in the heart is activated by $\alpha_1$-adrenergic and muscarinic receptors, endothelin and stretch (5). Compared with non-muscle tissues, the heart is insensitive to Ins(1,4,5)P$_3$ in terms of calcium release (6), with the addition of high concentrations of Ins(1,4,5)P$_3$ causing a slow leakage of calcium rather than the rapid release seen in most cells (7). In addition, Ins(1,4,5)P$_3$ enhances calcium oscillations which are associated with the development of arrhythmias (8, 9), but not calcium induced-calcium release, the mechanism involved in excitation-contraction coupling.

The present inventors have previously reported that PtdIns turnover pathway in the heart differs from that described in non-muscle cells. In heart, phosphorylation products of [$^3$H]Ins(1,4,5)P$_3$ are barely detectable, indicating reduced Ins(1,4,5)P$_3$ kinase activity (10). More recent studies have shown that little Ins(1,4,5)P$_3$ is released and metabolised either by phosphorylation or dephosphorylation and that most of the accumulated inositol phopshates derive from Ins(1,4)P$_2$ rather than Ins(1,4,5)P$_3$ (11). These findings suggest that Ins(1,4,5)P$_3$ does not play a major role in the healthy heart.

However, there is evidence that the PtdIns pathway and Ins(1,4,5)P$_3$ may be more important under pathological conditions such as myocardial ischaemia and reperfusion. $\alpha_1$-Adrenoceptor stimulation, which is associated with inositol phosphate release, is capable of inducing arrhythmias both ventricular tachycardia (VT) and ventricular fibrillations (VF) during both ischaemia and reperfusion. Such responses are not observed under normoxic conditions. Ischaemia has been reported to increase $\alpha_1$-adrenoceptor density in a number of myocardial preparations (12) as well as increasing responsiveness to noradrenaline stimulation (13). Reperfusion of ischaemic myocardium, is associated with large calcium accumulations, apparently associated with $\alpha_1$-adrenoceptor stimulation (14). These calcium accumulations have been implicated in reperfusion-induced injury. Furthermore, $\alpha_1$-adrenoceptor blockade, by a number of antagonists, has been shown to be anti-arrhythmic under both ischaemic and reperfusion condition (15).

In work leading to the present invention, detailed studies were carried out in isolated perfused rat hearts to determine and characterise the effects of ischaemia and reperfusion on the PtdIns turnover pathway, and to investigate a possible functional role for the second messenger Ins(1,4,5)P$_3$ under these pathological conditions.

It was surprisingly discovered that reperfusion with oxygenated medium after global ischaemia caused a rapid and quantitatively large rise in Ins(1,4,5)P$_3$ which could be correlated in time with the observed development of arrhythmias. Furthermore, it was observed that by blocking the formation of Ins(1,4,5)P$_3$ in the heart, using the aminoglycosides neomycin, gentamicin or streptomycin (being agents known to inhibit the formation of Ins(1,4,5)P$_3$) it was possible to completely abolish, or significantly reduce arrhythmias occurring following reperfusion of the ischaemic heart.

Accordingly, one aspect of the present invention contemplates a method for the prophylaxis or treatment of cardiac dysfunction in a mammal said method comprising administering to said mammal an effective amount of an agent capable of blocking formation or release of Ins(1,4,5)P$_3$ in cardiac tissue.

Another aspect of the present invention is directed to a pharmaceutical composition useful in the prophylaxis and/or treatment of cardiac dysfunction comprising an agent capable of blocking formation or release of Ins(1,4,5)P$_3$ in cardiac tissue together with one or more pharmaceutically acceptable carriers and/or diluents.

Yet another aspect of the present invention relates to an agent for use in blocking formation or release of Ins(1,4,5)P$_3$ in cardiac tissue.

Still yet another aspect of the present invention is directed to the use of an agent which blocks formation or release of Ins(1,4,5)P$_3$ in cardiac tissue in the manufacture of a medicament for the treatment or prophylaxis of cardiac arrhythmia.

Optionally another anti-cardiac dysfunction agent such as an anti-arrhythmic drug is administered in combination with agents which block or inhibit the effect or release of Ins(1,4,5)P$_3$ Such agents including, but not limited to, agents which induce thrombolysis for example, streptokinase and tissue plasminogen activator or other anti-arrhythmic agents for example, amiodorone, sotolol and lignocaine.

In a preferred embodiment, the mammal is a human, a livestock animal such as a sheep, cow, horse, donkey or pig or a laboratory test animal such as a mouse, rat, rabbit, guinea pig, cat or dog. Most preferably, the mammal is a human.

The term "cardiac dysfunction" is used in its most general sense and relates to any condition which causes a reduction in effective pumping action of the heart such that tissues are inadequately perfused. More particularly, it covers or may result from the following conditions: cardiac arrhythmia, cardiomyopathy, allograft rejection (cardiac), coronary angioplasty, cardiopulmonary by-pass surgery and electrophysiological studies. The present invention is particularly directed to the prophylaxis and/or treatment of cardiac arrhythmia. Reference hereinafter to cardiac arrythmia should be taken as covering all conditions contemplated above.

The present invention is described in detail hereafter in terms of the effect of $Ins(1,4,5)P_3$ inhibition in rat cardiac tissue. However, it is understood that it extends to the effect of the $Ins(1,4,5)P_3$ inhibitor in all mammals and in particular humans and livestock animals. Accordingly, any reference herein to the effect of $Ins(1,4,5)P_3$ inhibition in rats is meant to be applicable to the effect of $Ins(1,4,5)P_3$ inhibition in all mammals and in particular humans and livestock animals.

The term "cardiac arrhythmia" is used herein to denote conditions in a mammal where there is an irregular heart action caused by physiological or pathological disturbances in discharge of cardiac impulses or their transmission through the conducting tissue of the heart, and includes tachycardia and fibrillations of particular cardiac sites, including but not limited to, atrial, essential, nodal, paroxysmal atrial, paroxysmal nodal, paroxysmal ventricular, polymorphic ventricular, reflex and sinus and ventricular fibrillation. Accordingly, the treatment of cardiac arrhythmia is taken to be returning or maintaining the regular action of the heart by the administration of an effective amount of an agent which blocks or inhibits the effect or release of $Ins(1,4,5)P_3$ for a time and under conditions sufficient to maintain, or return, the regular action of the heart. Cardiac arrhythmia may occur following a disease condition or result from trauma or therapy and the present invention is not limited to any one or more causes of cardiac arrhythmia. Typically, cardiac arrhythmia will occur following myocardial infarction, as a consequence of reperfusion following cardio-pulmonary by-pass surgery, and in patients having unstable angina.

The present invention also extends to preventative therapy whereby an agent which blocks the effect or release of $Ins(1,4,5)P_3$ is administered to prevent or reduce the likelihood of cardiac arrhythmia developing.

The agents capable of blocking the effect or inhibiting the effect or release of $Ins(1,4,5)P_3$ which are used in accordance with the present invention include, for example:

(i) agents which affect the biochemical release of $Ins(1,4,5)P_3$ from the phospholipid $PtdIns(4,5)P_2$ to cause reduction in $Ins(1,4,5)P_3$ formation. Such agents include the class of compounds known as the aminoglycosides, for example; gentamicin, tobramycin, amikacin, netilimicin, kanamycin, streptomycin and neomycin or derivative thereof, and the class of compounds known as polyamines, for example; spermine or derivative thereof as well as agents which bind the phospholipase C (PLC) enzyme to produce inhibition; and (ii) agents which block the effects of $Ins(1,4,5)P_3$, for example, agents which block the $Ins(1,4,5)P_3$ receptor, or antagonist molecules to $Ins(1,4,5)P_3$.

Accordingly, in one preferred embodiment, the present invention provides a method for treating or preventing cardiac arrhythmias in a mammal which method comprises administering to said mammal an effective amount of an aminoglycoside for a time and under conditions sufficient to modulate cardiac arrhythmia.

Preferably the aminoglycoside is one of the group comprising gentamicin, tobramycin, amikacin, netilimicin, kanamycin, streptomycin, neomycin or derivatives thereof. Even more preferably the aminoglycoside is neomycin or derivative thereof. In a most preferred embodiment the amino glycoside is gentamicin.

In a further preferred embodiment the invention provides a method for treating or preventing cardiac arrhythmias in a mammal which method comprises administering to said mammal an effective amount of a polyamine molecule for a time and under condition sufficient to modulate cardiac arrhythmia.

Preferably, in this aspect of the invention the polyamine is spermine or its derivatives. In a more preferred aspect the polyamine is spermine.

Furthermore, the route of administration of the polyamine or aminoglycoside or other agent blocking or inhibiting the effect or release of $Ins(1,4,5)P_3$ is preferably by oral, parenteral or buccal administration but other routes may be equally applicable with only minor modifications to the methods contemplated herein. The effective amount of the agent will depend on the mammal and the condition to be treated, however, the amount to be administered to the mammal will need to be non-toxic. In general, the effective amount of agent will be a daily dose in the range of $0.1 \rightarrow 100$ mg/kg, more preferably 1–100 mg/kg and even more preferably 5–60 mg/kg.

Pharmaceutically acceptable carriers or diluents for use in the composition of this invention are well known to persons skilled in the art, and by way of example are described in Remington's Pharmaceutical Sciences, 18th Edition, Mack Publishing Company, Easton, Pa., USA.

The method and pharmaceutical compositions described in accordance with the present invention will be useful inter alia in the treatment or prevention of cardiac arrhythmias occurring as a result of various surgical procedures, or underlying cardiac disease.

Agents capable of blocking formation or release of $Ins(1,4,5)P_3$ are generally first tested in vitro in perfused heart tissue such as isolated perfused rat hearts. Potentially useful agents are then tested in vivo in a small animal model, such as rats, mice, guinea pigs or rabbits. Agents which are still of potential interest following this initial in vivo screen may then be tested in a larger animal model such as dogs, horses, pigs or mini-pigs. Clinical trials in human subjects may then follow using agents which still show signs of useful activity. A suitable protocol for clinical trials of anti-arrhythmic agents is described by Heidbuchel et al. (36).

The present invention is further described by the following non-limiting Figures and Examples.

In the Figures:

FIG. 1 is a diagrammatic representation of the phosphatidylinositol turnover pathway. The pathway predominating in heart is boxed.

FIGS. 2A and 2B show HPLC profiles of TCA extracted inositol phosphates from isolated perfused rat hearts. A: control heart; B: heart subjected to 30 minutes global myocardial ischaemia. Long arrows indicate elution position of nucleotide standards.

FIGS. 3A–C are graphical representations showing the accumulation of $^3H$-labelled inositol phosphates in cpm/mg protein in isolated perfused rat hearts subjected to increasing periods of global myocardial ischaemia.

FIGS. 4A–C are graphical representations showing the accumulation of $^3H$-labelled inositol phosphates in isolated perfused rat hearts subject to ischaemia and subsequent reperfusion following a 20 minute ischaemic period.

FIGS. 5A–I are graphical representations showing accumulation of individual $^3H$-labelled inositol phosphates in isolated perfused rat hearts subject to noradrenaline stimulation (A–C) ischaemia and reperfusion (D–F) and ischaemia and reperfusion in the presence of reserpine (G–I).

FIGS. 6A–D are graphical representations showing the effect of various neomycin concentrations on $^3$H-labelled inositol phosphate accumulation within 2 minutes reperfusion following 20 minutes global ischaemia as a percentage of untreated 2 minutes reperfusion response.

EXAMPLE 1

Inositol Phosphate Experiments

The inositol phosphate response in heart

Figure 1:
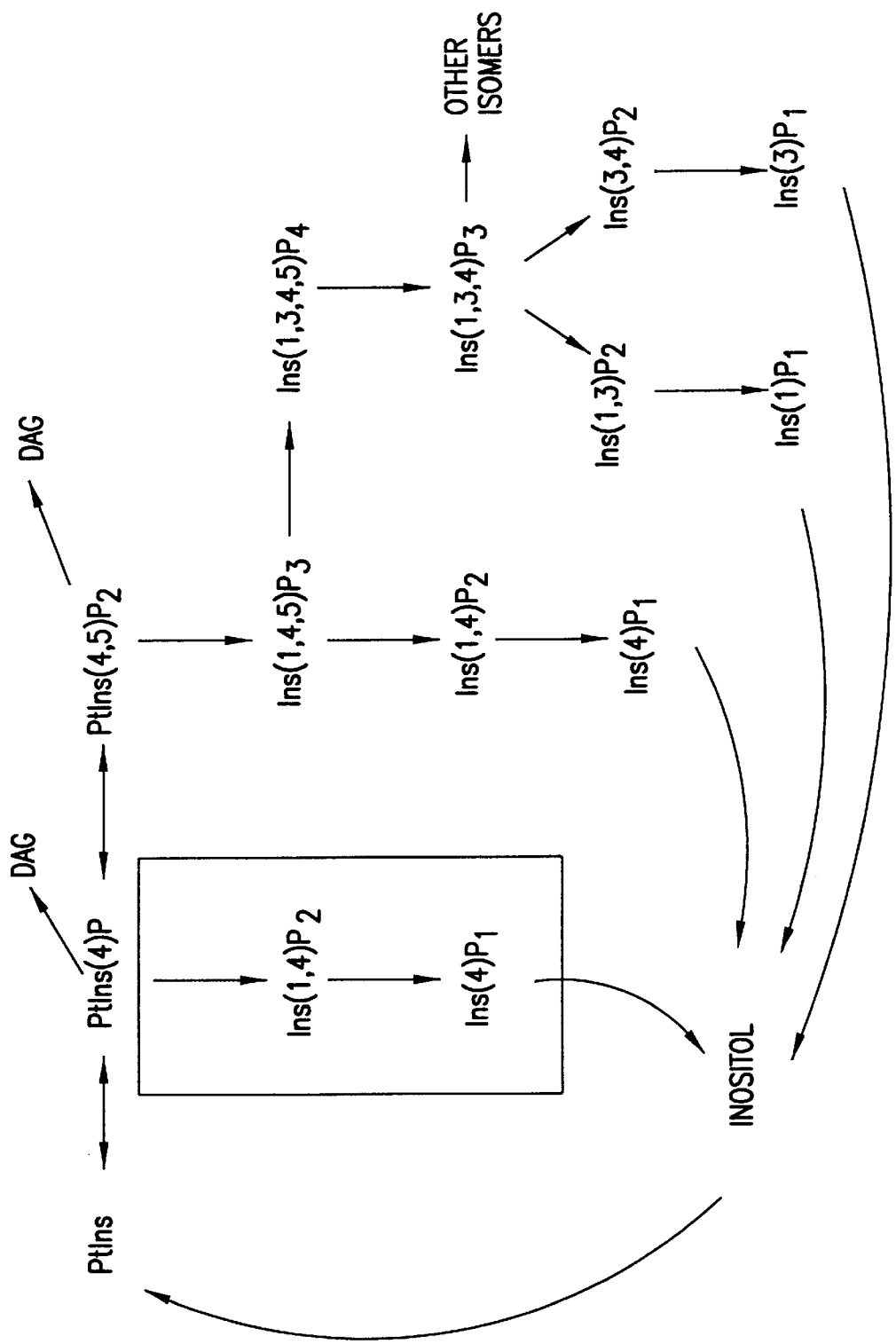

Earlier studies in the inventors' laboratory showed that the pathway of inositol phosphate release and metabolism in heart tissue was different from that in other cells in that products of dephosphorylation of the $Ca^{2+}$-releasing messenger Ins(1,4,5)P$_3$ were observed but the phosphorylation products were not (10). The metabolic pathways involved are shown in FIG. 1. Subsequent studies provided an explanation for these findings by demonstrating that the primary release product of phosphatidylinositol-specific phospholipase C (PLC) in heart was Ins(1,4)P$_2$ rather than Ins(1,4,5) P$_3$ (11). This suggested that heart tissue avoided the generation of Ins(1,4,5)P$_3$ and provided the basis for the current studies. More recent studies have provided a mechanistic basis for this unusual pathway by showing that the "cardiac" pathway correlates with the presence of an atypical GTP-binding coupling protein called Gh (16). Gh couples to a different phospholipase C from PLC-P which couples receptors to typical GTP-binding proteins (17). To further test the association of Gh with the cardiac inositol phosphate pathway, effects of an inhibitor of PLC-β was investigated (18). This compound, U-73122, did not inhibit the accumulation of inositol phosphates in heart tissue under noradrenaline stimulation but was a fully effective inhibitor in isolated neonatal cardiomyocytes which lack Gh and have an inositol phosphate metabolic pathway indistinguishable from non-muscle cells. Thus, the phosphatidylinositol turnover pathway in heart tissue differs from that in other cell types in a number of important aspects.

The inventors investigated the possibility that some alteration in the pathway was responsible for the arrhythmic action of $α_1$-adrenergic agonists under conditions of myocardial ischaemia and reperfusion.

A) Methods

Inositol phosphate response in isolated perfused rat hearts

Adult male sprague dawley rats 250–300 g were used. Where indicated, rats were treated with reserpine (5 mg/kg I.P. for 18 hrs prior to killing) to deplete endogenous noradrenaline stores.. Rats were heparinized 1 U/g I.P. 30 minutes prior to killing by decapitation. Hearts were rapidly excised and immediately chilled in ice-cold saline. Under ice-cold solution, hearts were cannulated via the ascending aorta as described by Langendorff and perfused retrogradely at a rate of 5 ml/min with HEPES-buffered Krebs solution equilibrated with 5%$CO_2$-95%$O_2$ at 37° C. Initial perfusion was in a non-recirculating manner to remove internal blood. Hearts were allowed to warm up gradually and, when free of internal blood, transferred to a 37° C. water-jacketed organ bath containing carbogenated Krebs medium, and perfusion continued in a recirculating manner. Following a 15 minute equilibration period, hearts were labelled with [$^3$H]-inositol, 2 μCi/ml for 2 h. Hearts were monitored throughout the labelling period for strong rhythmic beating. Any hearts which did not fulfil these requirements were discarded.

Following labelling, the [$^3$H]-inositol-containing medium was removed, and replaced with Krebs medium containing propranolol ($10^{-6}$ M) and lithium chloride (50 mM) to block β-adrenergic receptors and to inhibit InsP metabolism by InsP 1'-phosphatase respectively (20). Hearts were perfused with propranolol, LiCi solution for 10 minutes prior to ischaemia. Antagonists, when administered, were included in this 10 minute preincubation. Normothermic global ischaemia was induced by terminating perfusion for various times up to 30 minutes. Reperfusion was examined following a 20 minute ischaemic period by resuming perfusion at 5 ml/min. Reactions were terminated by freezing hearts in liquid $N_2$ following excision at the atrioventricular junction. Frozen ventricles were weighed and inositol phosphates extracted as described below.

Extraction of inositol phosphates

Inositol phosphates were extracted from ventricle samples in 3.5 ml ice-cold 5% trichloroacetic acid (TCA), 2.5 mM EDTA, 5 mM phytate solution, as described previously (21). Briefly, ventricles were homogenised with two 10 second passes of a "Polytron" homogenizer separated by 15 second periods on ice. Samples were homogenised further using a Potter-Elvejheim homogeniser followed by brief sonication. Homogenised samples were centrifuged (5000 rpm, 10 min, 4° C.) to remove TCA insoluble material. Supernatants were collected, and the remaining pellet re-extracted in 1.5 ml TCA, EDTA, phytate. Supernatants were pooled and freon, tri-n-ocylamine (1:1 v/v 0.75 ml:1 ml TCA solution) was added, mixed thoroughly, and phases separated by low speed centrifugation (2000 rpm, 10 min 4° C.). The resultant aqueous phase, containing inositol phosphates was collected and treated with proteinase K (50 μg/ml, 2 hr, 50° C.). This process was necessary to preserve the chromatography column. Treated samples were passed through a 1 ml Dowex-50 column (4% cross-linked 4–400 mesh size) and eluted with 1 ml water (22). Urea (0.05 M final) was added (23) and samples lyophilized prior to high performance liquid chromatography (HPLC) analysis. Recovery of inositol phosphates using this method was greater than 95% for each isomer, as estimated by addition of [$^3$H]-labelled standards to extractions of unlabelled hearts.

Separation and quantitation of inositol phosphates

Inositol phosphates were separated by an anion-exchange HPLC system using a Whatman Partisil 10μ SAX column in a Waters Radial Compression Unit, employing a complex ammonium phosphate gradient, pH 3.8 from 0–2 M as described previously (24). Inositol phosphates were detected and quantitated using an on-line P-counter (model CR, Radiomatic Instruments) All peaks were identified by comparison with commercial standards. Nucleotide standards AMP, ADP, and ATP were run with samples to assess column performance.

Noradrenaline determination in heart perfusate

Aliquots of heart perfusate for noradrenaline estimation were collected from ischaemic tissue and at various intervals of reperfusion following 20 minutes MI. Samples were analysed by HPLC and quantitated by electrochemical detection as described previously. (25).

Ins(1,4,5)P$_3$ Mass Analysis

Mass of Ins(1,4,5)P$_3$ was measured using a competitive binding assay (Amersham TRK 1000) essentially as described previously (26). Ventricle samples were prepared as described above except for the omission of [$^3$H]-label during the 2 hr perfusion of hearts prior to ischaemia, and for the use of 5 mm ATP instead of phytate in the extraction procedure. 5 mm phytate was found to cross-react in the Ins(1,4,5)P$_3$ assay.

Protein Determination

Protein concentration was determined in aliquots of TCA pellet following InsP extraction using a modified Lowry method with Bovine Serum Albumin as a standard.

Statistics

Values presented are mean ±SEM, for n=4 unless otherwise stated. Statistical analysis of results involved Students' unpaired "t-test" for all InsP data.

B) Results

Figure 2A:
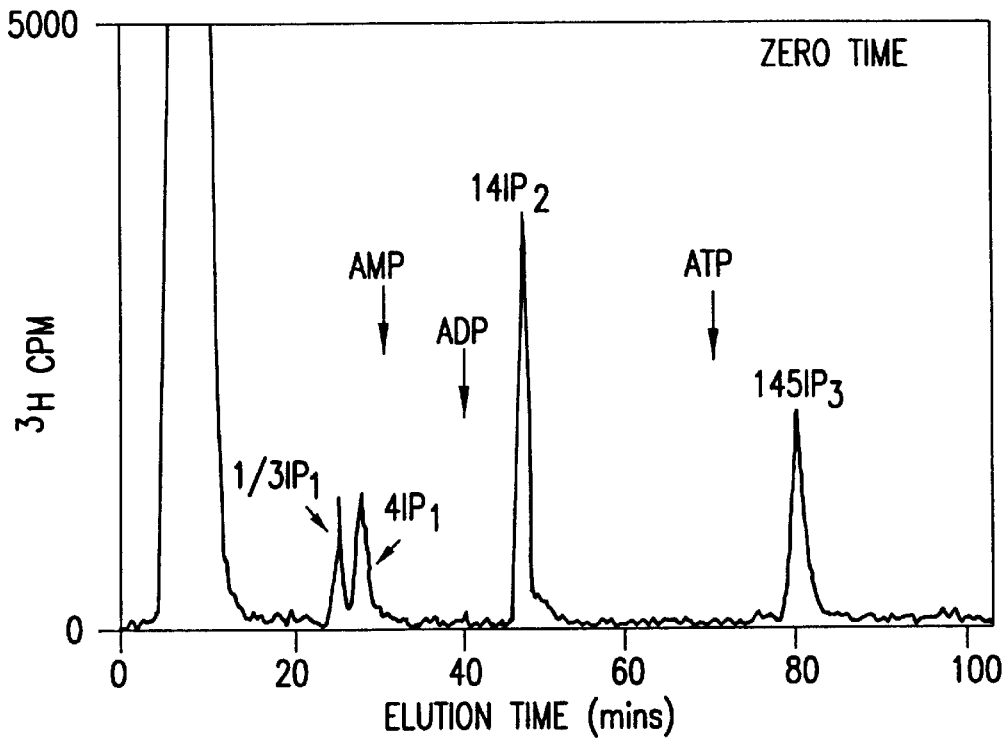
Figure 2B:
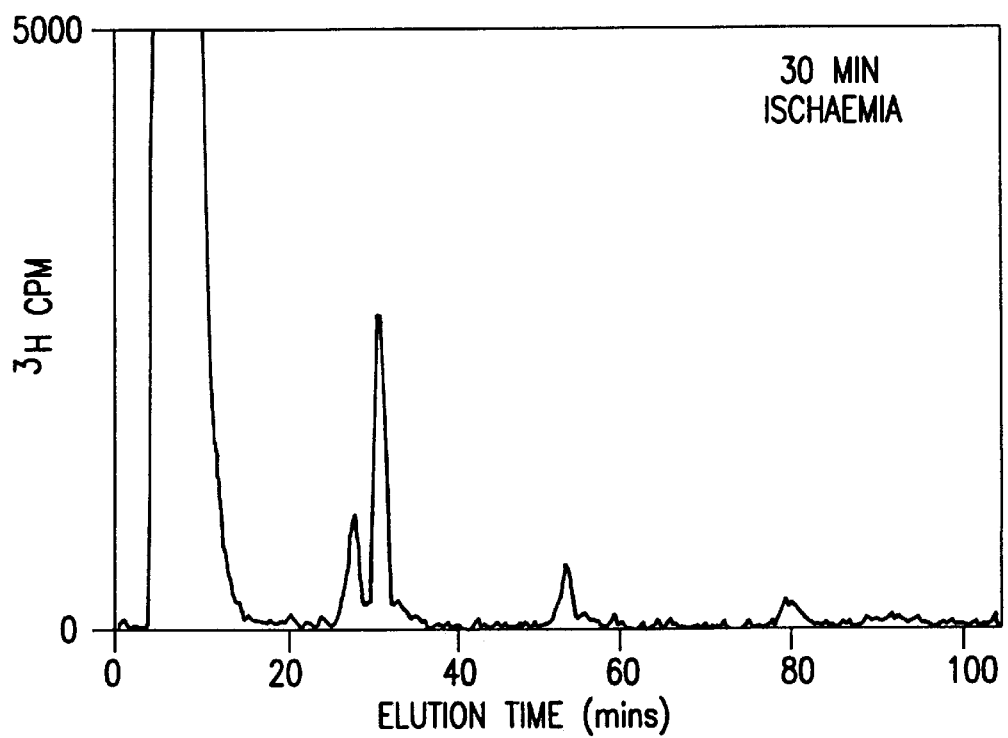
Figure 3A:
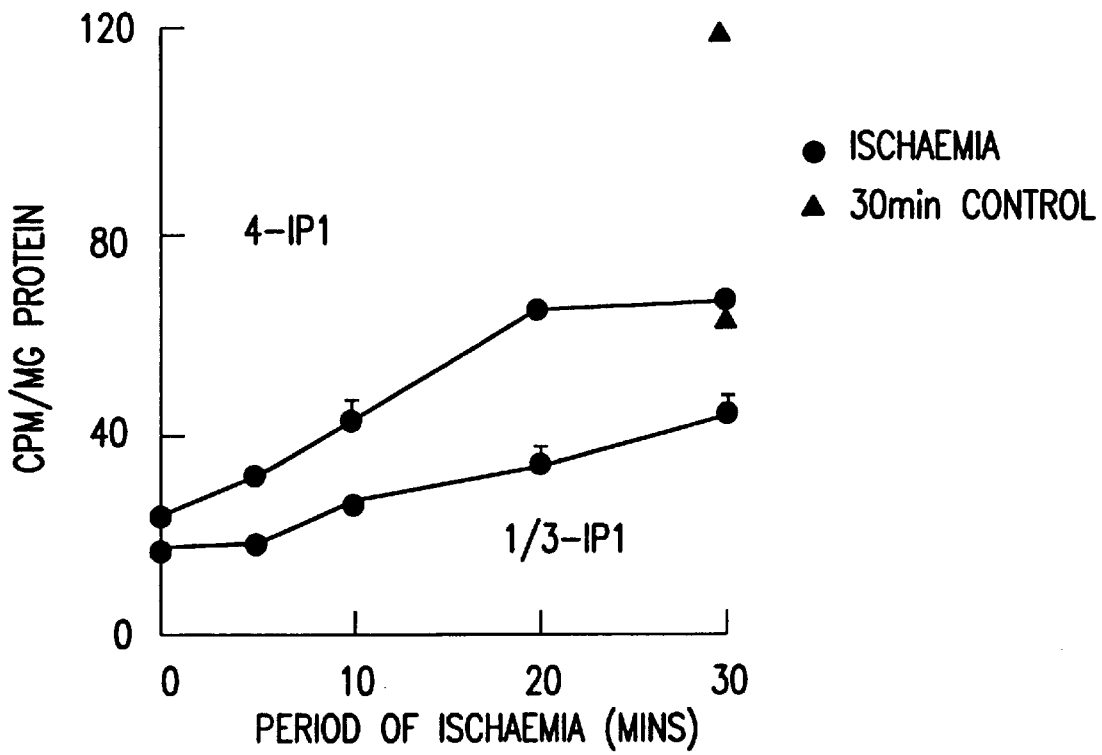
Figure 3B:
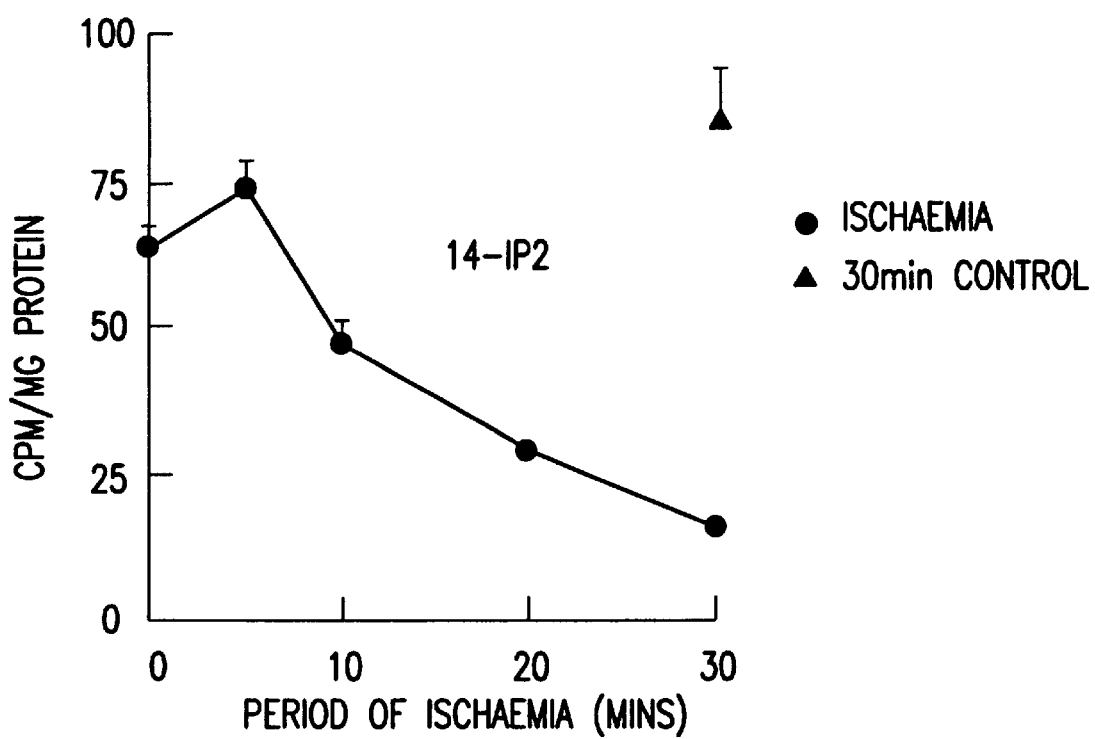
Figure 3C:
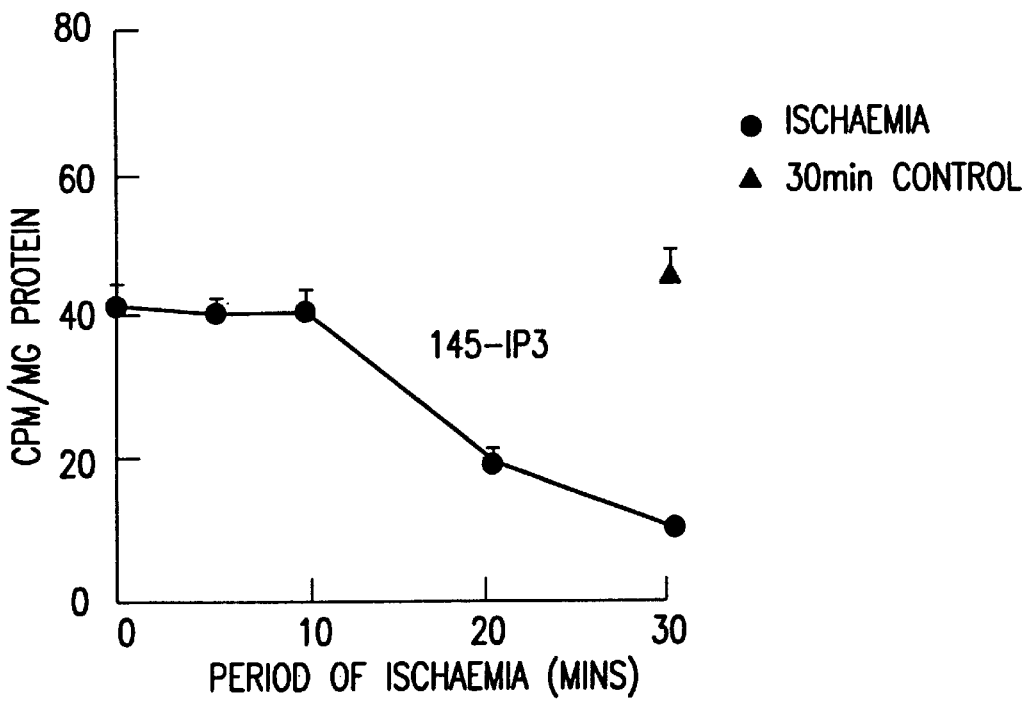

Effects of global ischaemia on the accumulation of [$^3$H]-labelled inositol phosphates TCA extracts of [$^3$H]inositol-labelled hearts contained compounds identified as Ins(⅓)P$_1$, Ins(4)P$_1$, Ins(1,4)P$_2$ and Ins(1,4,5)P$_3$. As reported previously, [$^3$H]Ins(1,3,4,5)P$_4$ and its metabolic products were not evident (FIG. 2a). Thirty minute perfusion with oxygenated medium resulted in a time dependent increase in [$^3$H]-label in inositol phosphates (FIGS. 3A–C). In contrast, global ischaemia caused an altered distribution of inositol phosphates (FIG. 2b), while the total amount of label remained unchanged. As shown in FIGS. 3A–C, decreases in Ins(1,4)P$_2$ and Ins(1,4,5)P$_3$, were observed together with concurrent increase in the degradation products Ins(l)P$_1$ and Ins(4)P$_1$. Significant changes in [$^3$H]-labelled inositol phosphates were observed after 5 min of ischaemia. The redistribution process observed under ischaemic conditions was independent of the endogenous noradrenaline released during ischaemia, as it was unaffected by both depletion of noradrenaline stores by reserpinization, or by α$_1$ adrenoceptor blockade with prazosin.

In contrast to normoxic perfusion, total accumulation of inositol phosphates in myocardium remained unchanged throughout the 30 minute ischaemic period studied, such that the decreases in [$^3$H]-label of Ins(1,4,5)P$_3$ and Ins(1,4)P$_2$ could be accounted for by increases in the metabolic products Ins(⅓)P$_1$ and Ins(4)P$_1$. These data indicate that global ischaemia causes an inhibition of PtdIns-PLC activity, such that no inositol phosphate release occurs, even in the presence of locally high concentrations of noradrenaline.

Control of inositol phosphate release under ischaemic conditions

More recent modelling studies have shown that the altered metabolism of inositol phosphates durong ischaemia is not related either to the reduced pH or the high ambient extracellular K$^+$ concentration, under these conditions. Rather, our studies indicated that the change in inositol phosphate profiles could be explained solely by the decrease in ATP content. Moderate anoxia reduced ATP content from 8.3±1 μmoles/g dry weight to 4.5±0.4 (mean±SEM, n=3, p<0.01) and this resulted in a reduction in content of Ins(1,4)P$_2$. Larger reductions in ATP (to 0.718±0.14), as occurs in global ischaemia, resulted in reduced Ins(1,4,5)P$_3$ as well as Ins(1,4)P$_2$. Both profiles, moderate and severe ischaemia, could be modelled using inhibitors of ATP generation.

Under conditions of moderate ischaemia, release of Ins(1,4,5)P$_3$ occurs in response to noradrenaline, the ambient levels of which are high under these conditions. Reperfusion following moderate ischaemia further enhanced this response (see below). Thus, whether Ins(1,4,5)P$_3$ release occurs under ischaemic conditions depends on the ATP content of the tissue and thus on the severity of the ischaemia. However, enhanced release is always observed with reperfusion.

Figure 4A:
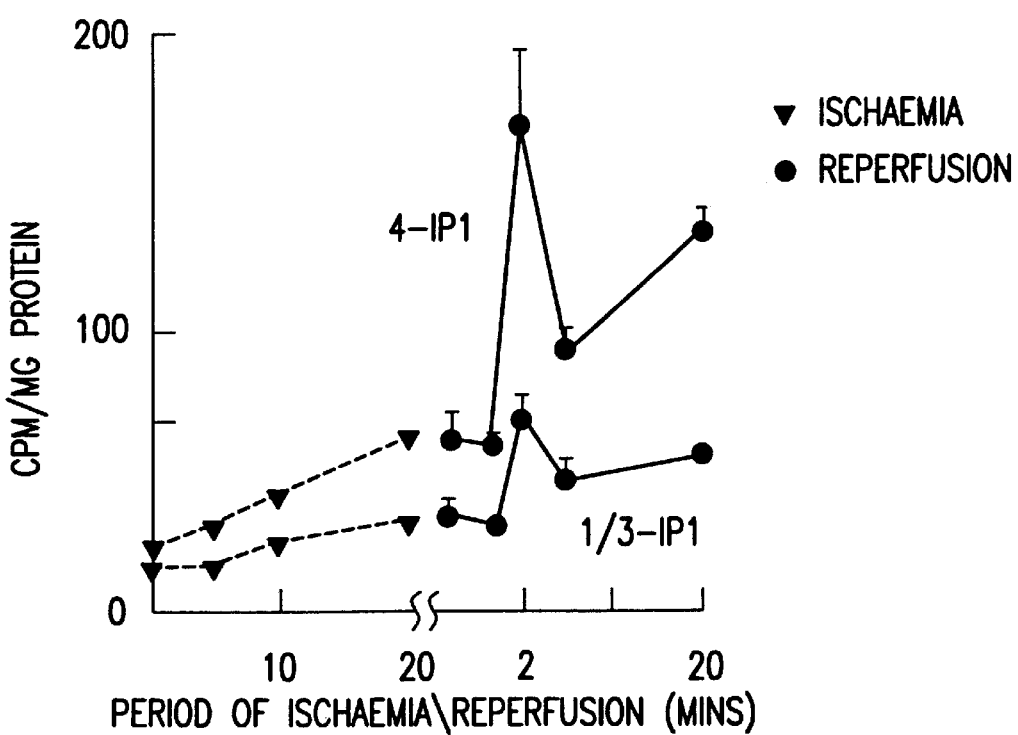
Figure 4B:
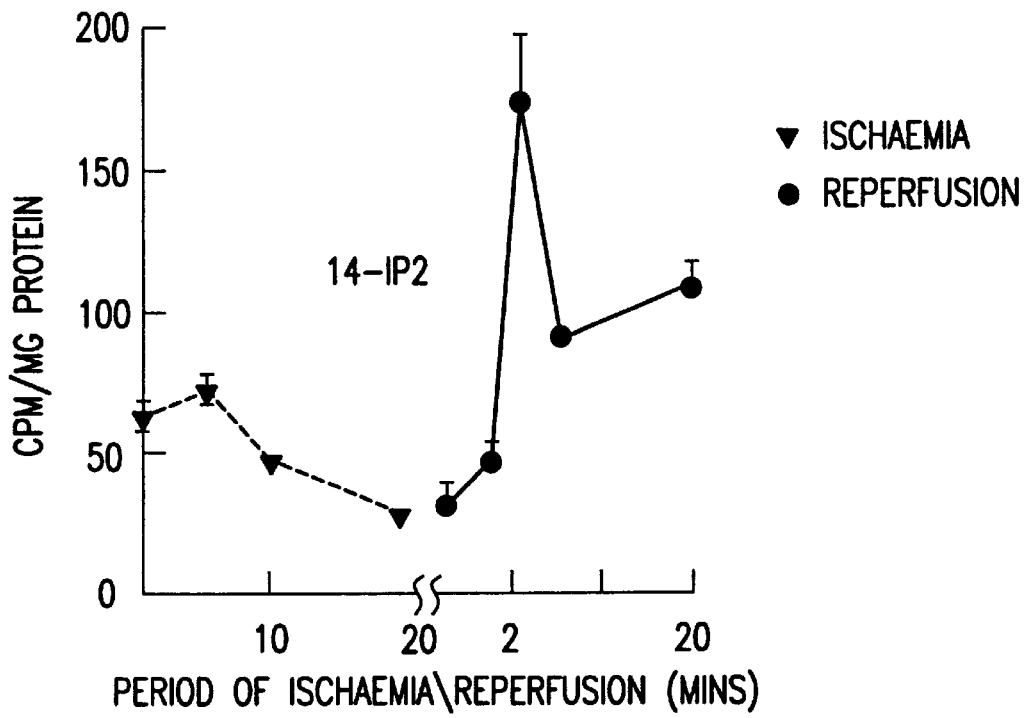
Figure 4C:
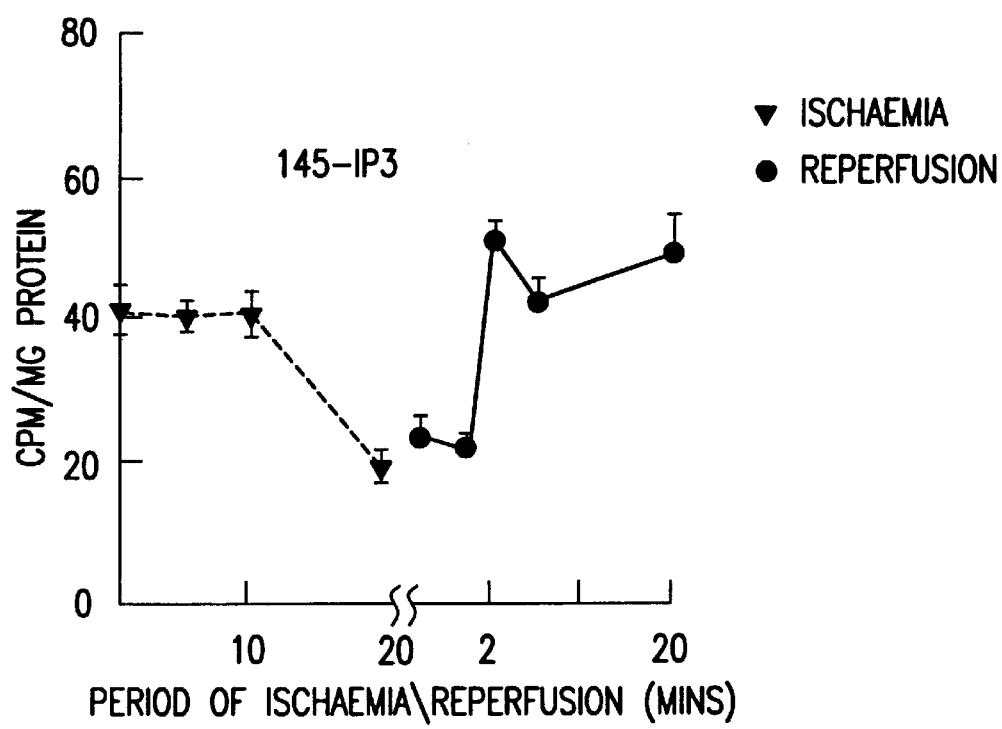

Effects of post-ischaemic reperfusion on the accumulation of $^3$H-labelled inositol phosphates Reperfusion with oxygenated medium following 20 minutes global myocardial ischaemia resulted in a rapid increase in accumulation of [$^3$H]-labelled inositol phosphates. This activation was biphasic, with a rapid and transient accumulation occurring between 1 and 2 minutes reperfusion, followed by a slow, quantitatively smaller, secondary accumulation which continued past 20 minutes (FIGS. 4A–C).

Figure 5A:
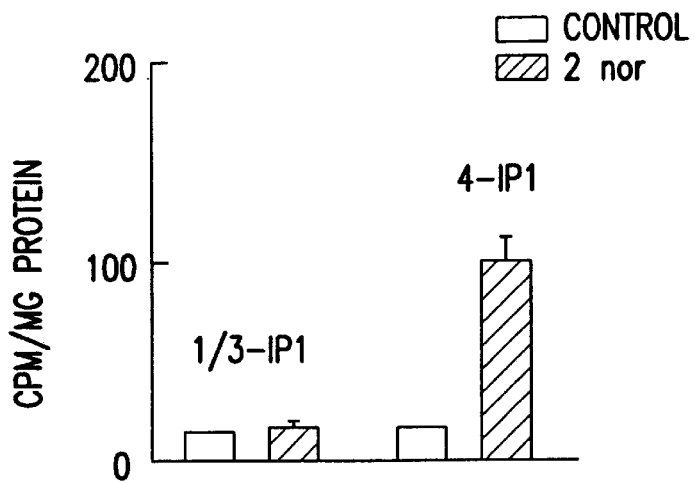
Figure 5B:
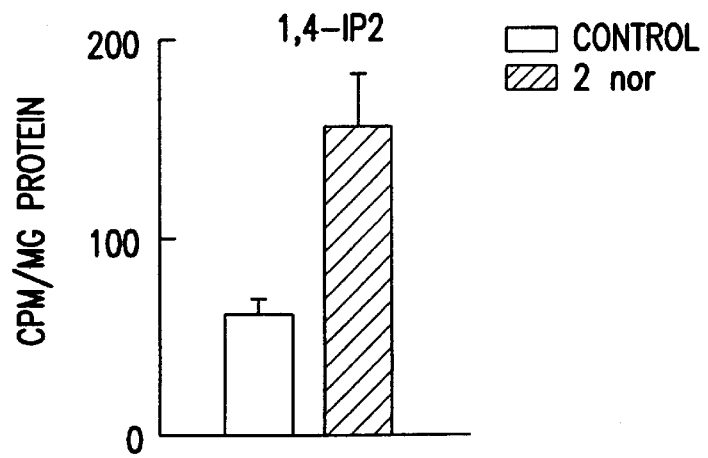
Figure 5C:
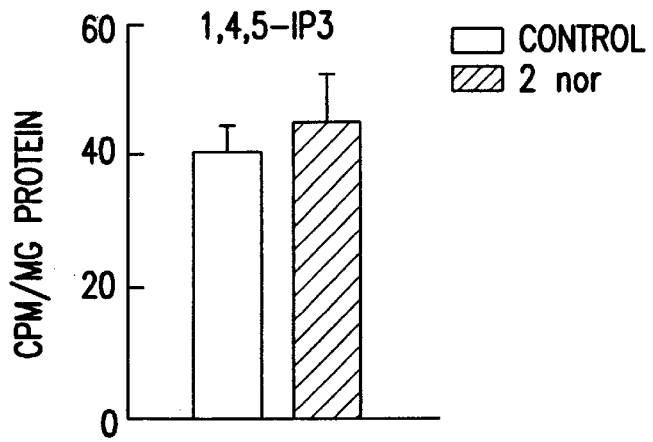
Figure 5D:
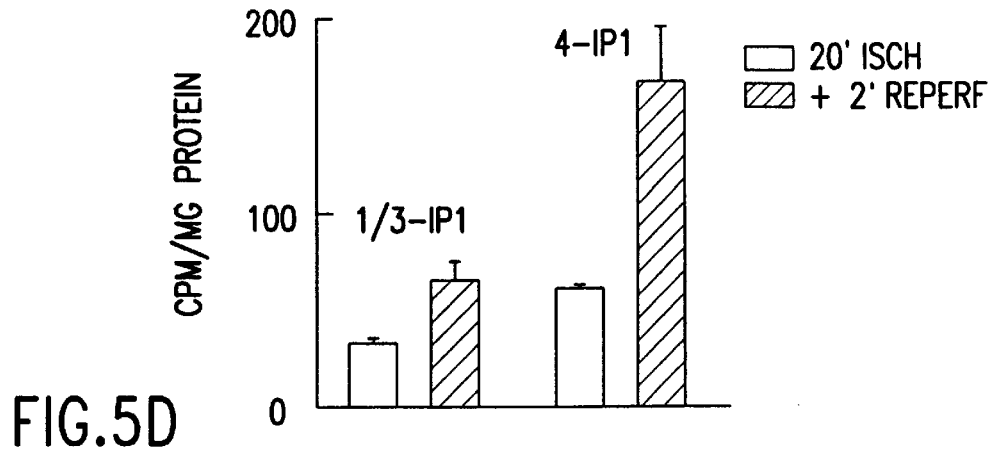
Figure 5E:
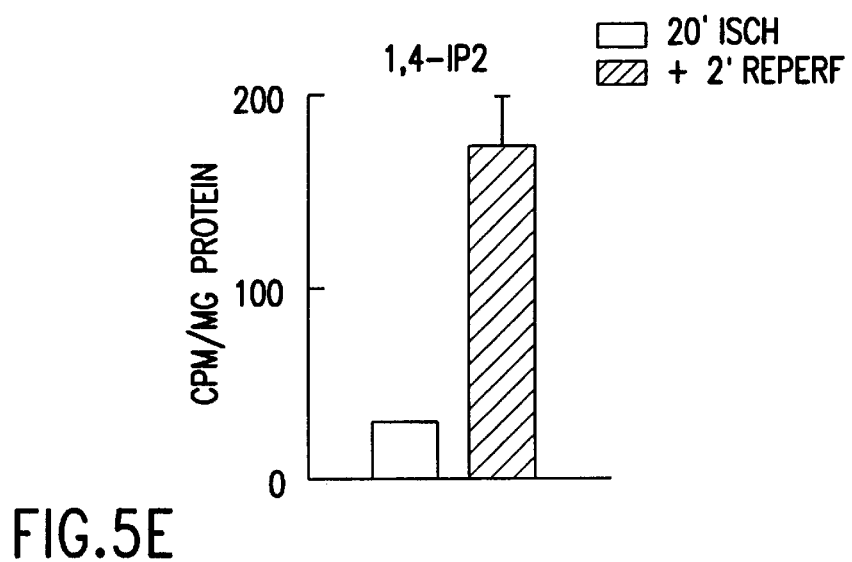
Figure 5F:
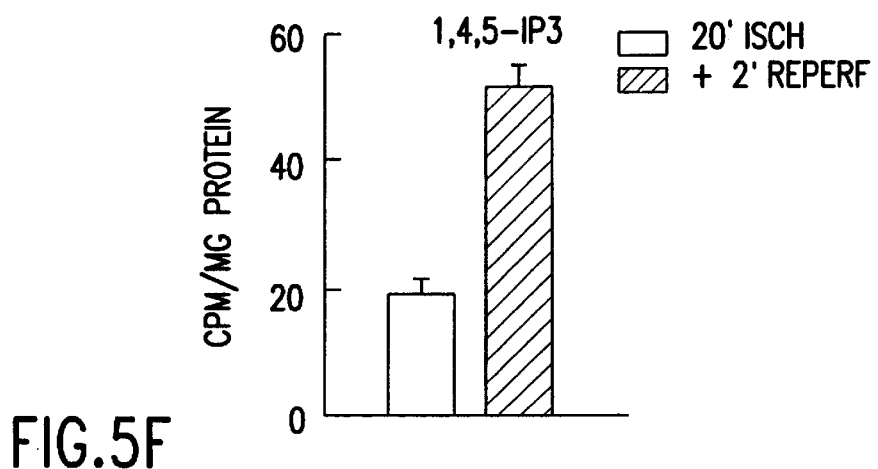
Figure 5G:
Figure 5H:
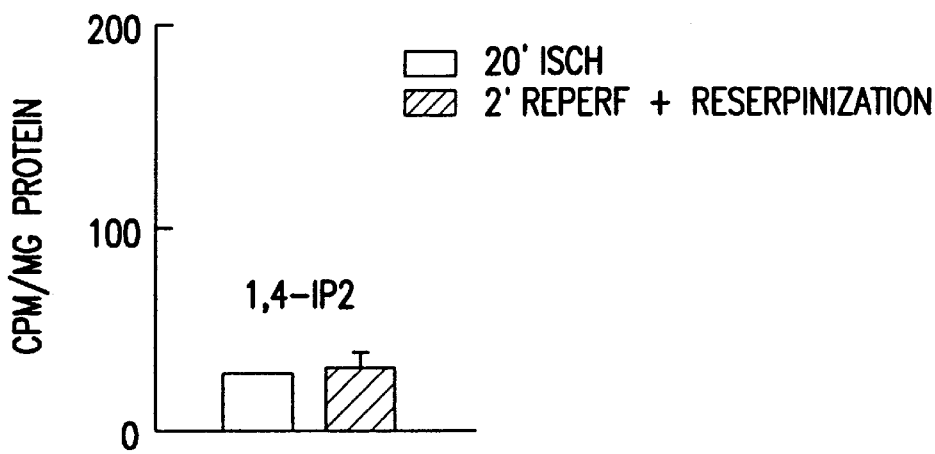
Figure 5I:
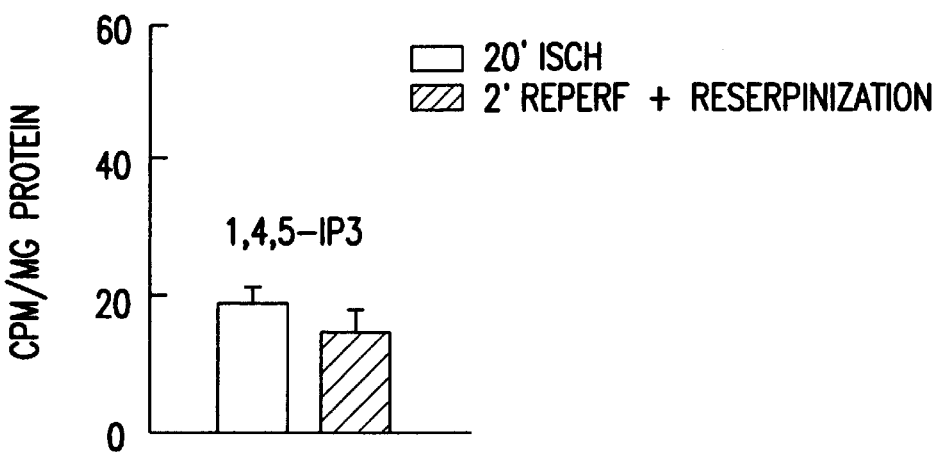
Figure 6A:
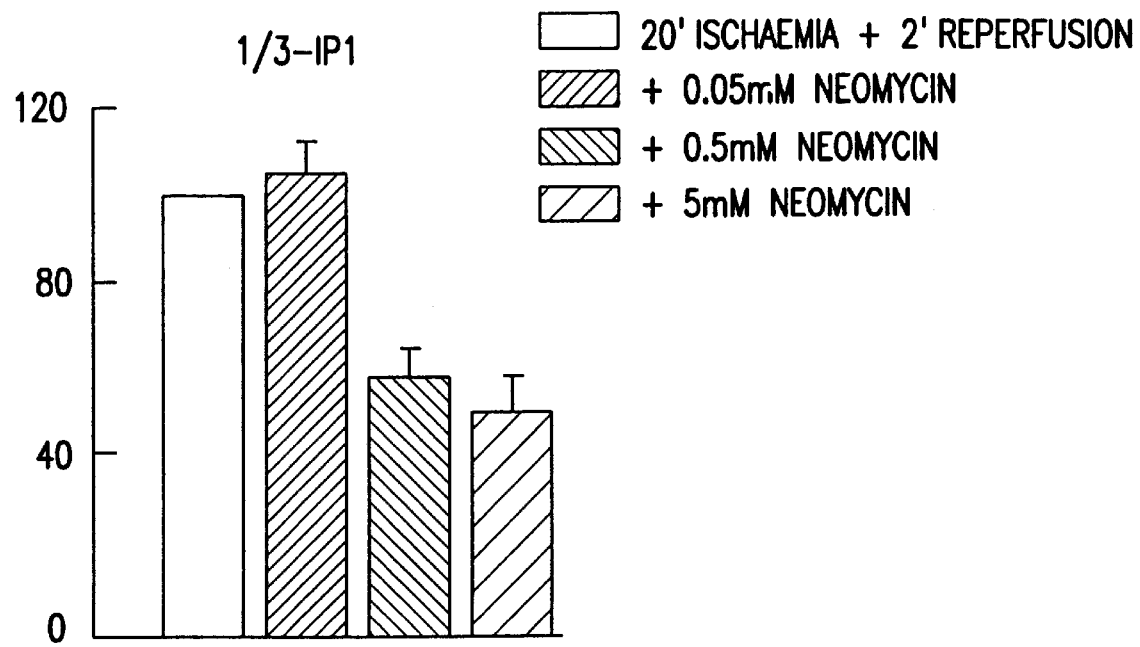
Figure 6B:
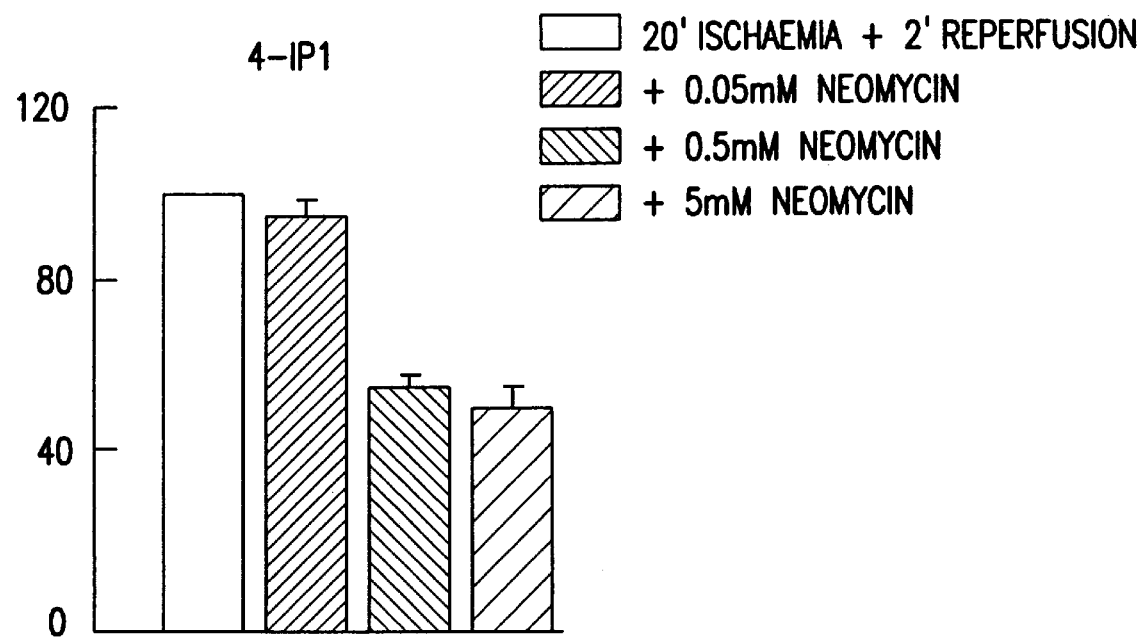
Figure 6C:
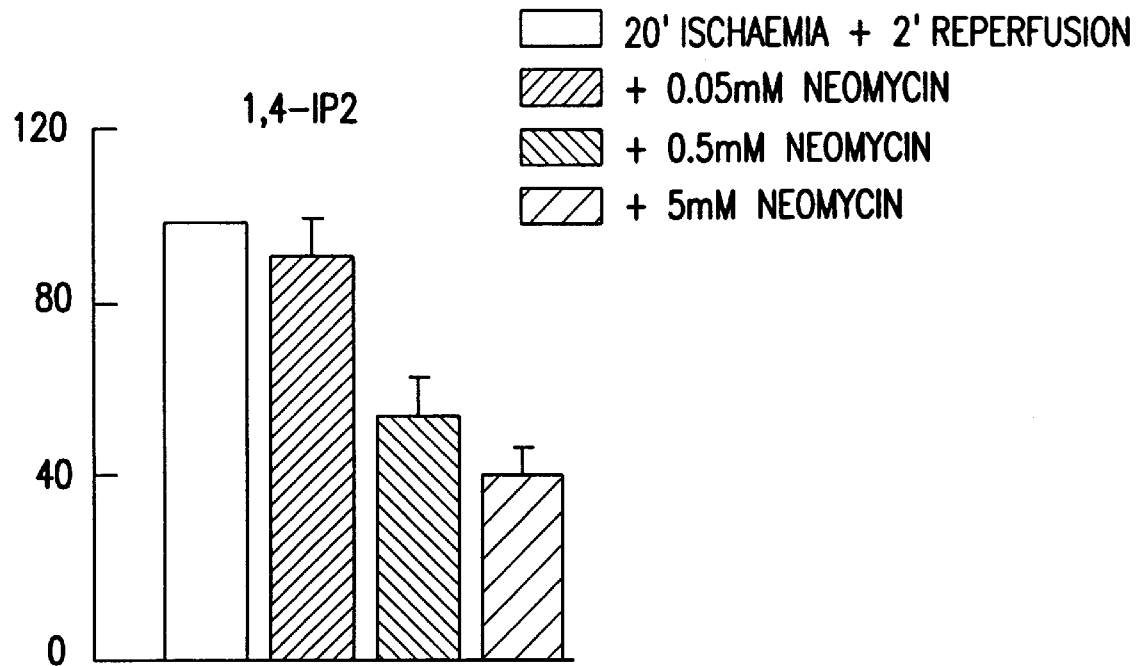
Figure 6D:
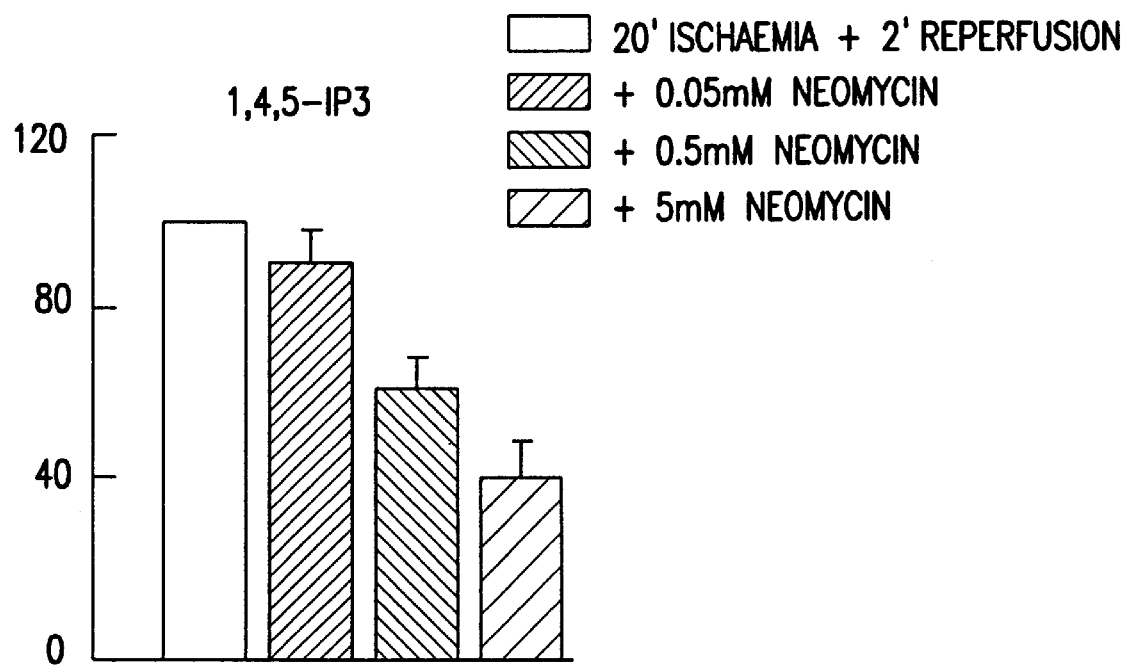
Figure 7:
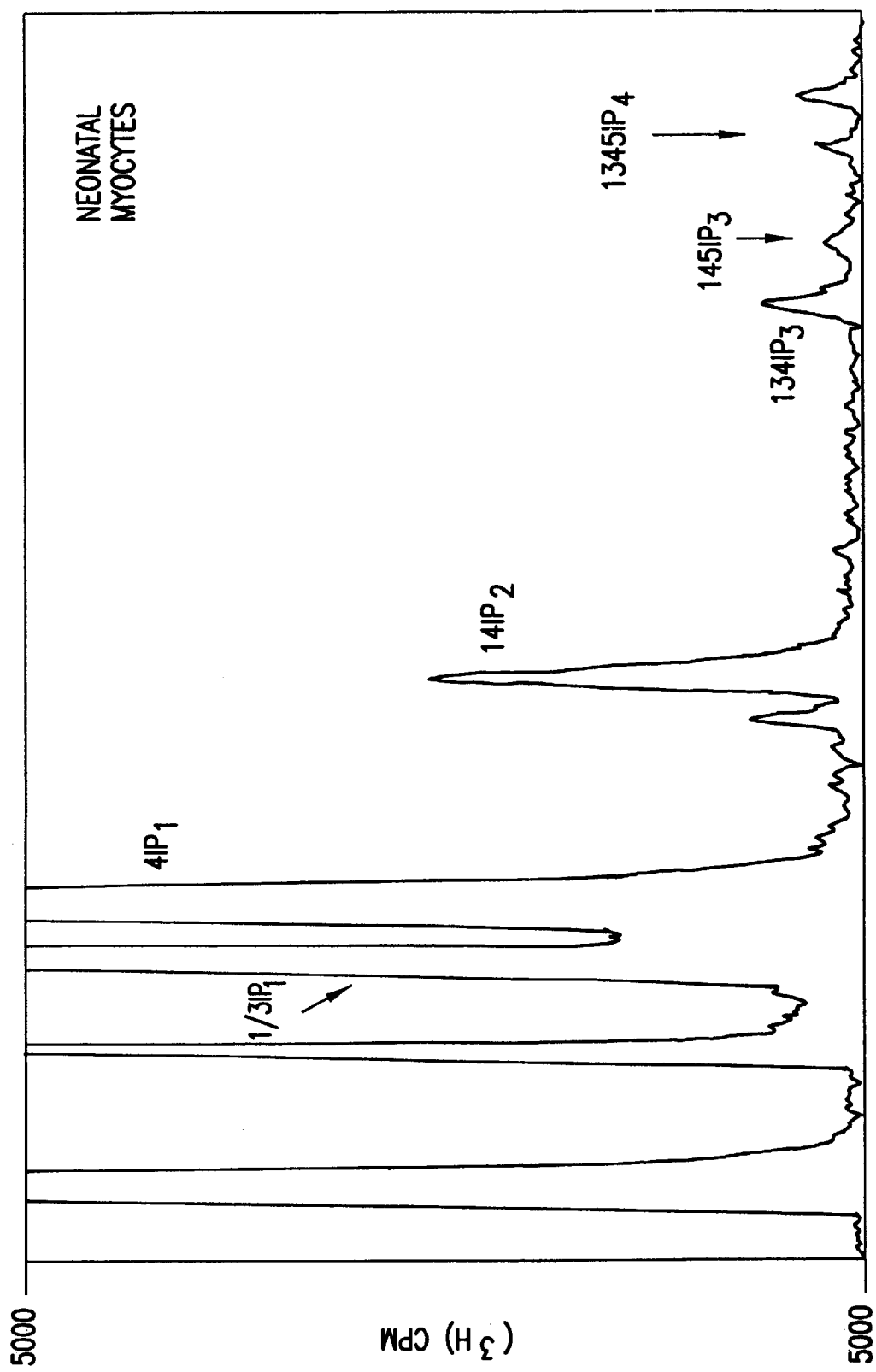
FIG. 7 is a graphical representation showing the accumulation of $^3$H-labelled inositol phosphates in cpm in neonatal myocytes. Note the low levels of Ins(1,4,5)P$_3$.
Figure 8:
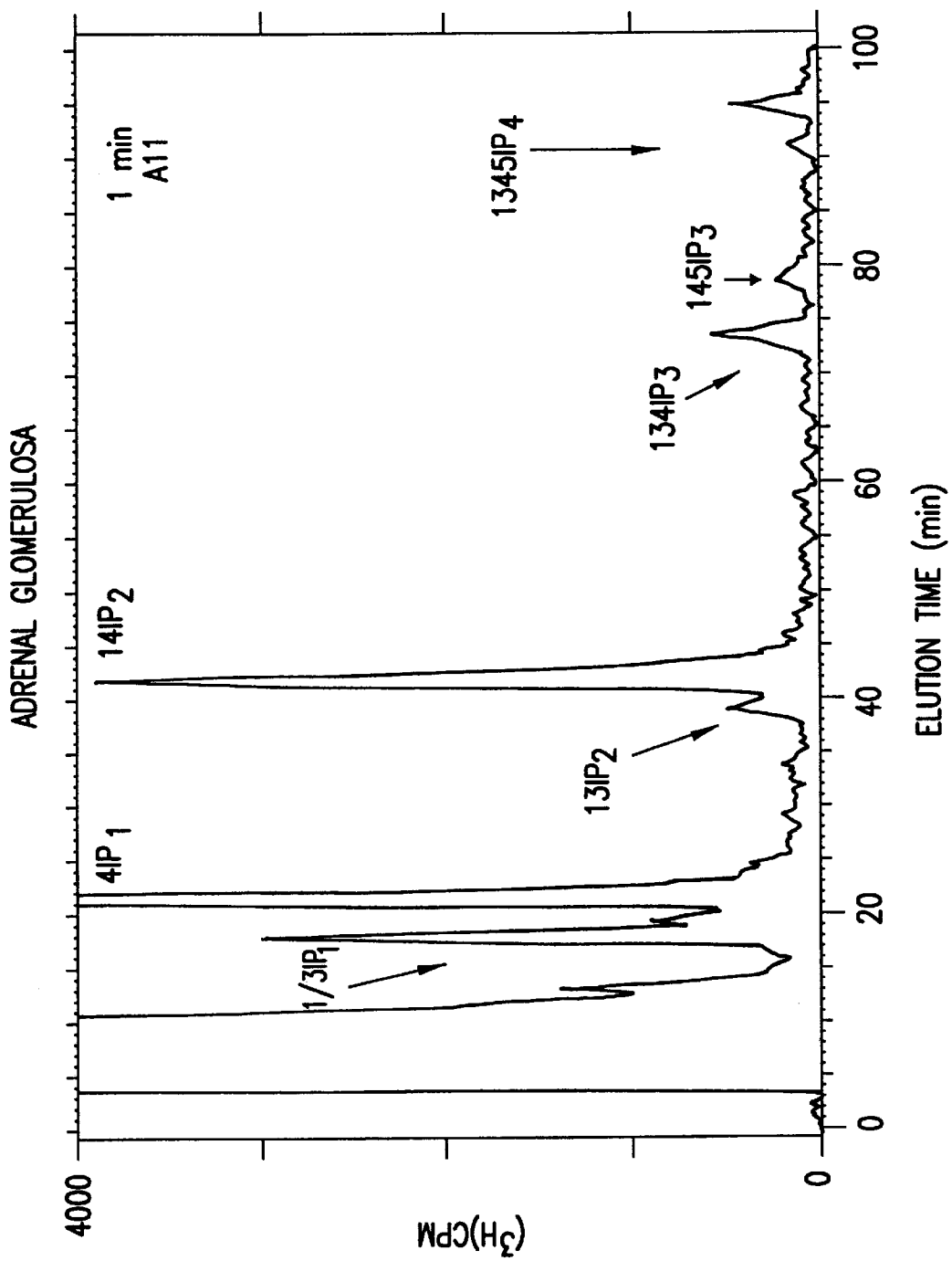
FIG. 8 is a graphical representation showing the accumulation of $^3$H-labelled inositol phosphates cpm in adrenal glomerulosa cells. Note the low levels of Ins( I ,4,5)P$_3$.

The rapid accumulation of inositol phosphates caused by 2 minutes post-ischaemic reperfusion was dependent on the release of endogenous noradrenaline, as it was prevented by prior reserpine treatment (FIGS. 5G–I). The release of [$^3$H]-labelled Ins(1,4,5)$_3$ could be reinstated in reserpinized animals by perfusion with 10$^{-4}$ M noradrenaline. Prazosin (10 μM) treatment inhibited the 2 minute reperfusion inositol phosphate response, demonstrating mediation via α$_1$-adrenoceptors. Thus, the immediate reperfusion Ins(1,4,5)P$_3$ response requires neuronally released noradrenaline and is mediated by α$_1$-adrenoceptors.

Even though the reperfusion Ins(1,4,5)P$_3$ response was caused by noradrenaline stimulation of α$_1$-adrenoceptors, it differed from the noradrenaline response under normoxic conditions in a number of ways. First, the release of inositol phosphates was quantitatively greater. Second, the profile of released inositol phosphates was different in that the primary release product under reperfusion conditions was Ins(1,4,5)P$_3$ whereas Ins(1,4)P$_2$ predominates under normoxic conditions (11). Third, inositol phosphate release under reperfusion conditions was inhibited by a number of compounds which did not inhibit release under normoxic conditions, as discussed in detail below (Table 1).

The 2 minute reperfusion response required the reintroduction of oxygen, as reperfusion with O$_2$ free (N$_2$ saturated) medium, did not activate inositol phosphate release. This finding is of great interest as recent reports indicate that oxidants increase the sensitivity of Ins(1,4,5)P$_3$ receptors (27). Thus, by two different mechanisms, increased release and increased sensitivity, Ins(1,4,5)P$_3$ can be more effective and more damaging under conditions of ischaemia and reperfusion.

Noradrenaline concentration under conditions of ischaemia and reperfusion

Endogenous noradrenaline is known to accumulate in myocardial extracellular space under ischaemic conditions (28). In the current studies the noradrenaline concentration was measured in the tissue and surrounding perfusate, to verify such accumulation in the inventors' model. Control values (9.87±1.54×10$^{-10}$ M) were sampled following 10 minutes recirculating perfusion with Krebs' medium containing propranolol and LiCl prior to initiation of ischaemia. 20 minutes global ischaemia caused an accumulation of noradrenaline within the myocardial extracellular space (8.19±2.03×10$^{-7}$ M). This noradrenaline was released rapidly with reperfusion and levels remained elevated at 2 minute reperfusion (1.26±0.28×10$^{31\ 8}$ M), although diluted around 40 fold when released into the 10 ml recirculating perfusate. Perfusate noradrenaline levels dropped significantly following 20 minutes reperfusion (1.06±0.5×10$^{-9}$ M) to a level not different from those of controls (P>0.3). Noradrenaline concentrations in the perfusate after 2 minutes reperfusion averaged 1.54±0.5×10$^{-8}$ M. Such concentrations are not effective in stimulating inositol phosphate release from non-ischaemic myocardium. This demonstrates an increased sensitivity or availability of ventricular $\alpha_1$-adrenoceptors during 2 minutes post-ischaemic reperfusion. Previous studies in the inventors' laboratory have shown that nerve stimulation of non-ischaemic myocardium produces little increase in Inositol phosphate accumulation. Thus, cardiac $\alpha_1$-adrenoceptors responds to neuronally released noradrenaline only under conditions of ischaemia and reperfusion.

Effect of aminoglycosides on the reperfusion- induced [$^3$H]-labelled Inositol phosphate response The aminoglycoside antibiotic neomycin has been well characterised as an inhibitor of Ins(1,4,5)P$_3$ release (29)(30). The effects of neomycin on the 2 minute reperfusion-induced [$^3$H]-labelled Inositol phosphate response were investigated. Neomycin (0.05 mM), added 10 minutes prior to ischaemia and maintained throughout the procedure, did not significantly inhibit the accumulation of [$^3$-H]-labelled inositol phosphates. Higher concentrations, 0.5 mM and 5 mM, produced a 45% and 55% average inhibition of [$^3$H]-labelled Inositol phosphate accumulation respectively, compared with 2 minutes post-ischaemic reperfusion in the absence of neomycin (FIG. 6). These results are different from findings in healthy heart tissue where 5 mM neomycin caused a 20% reduction in accumulation of [$^3$H]Ins(1,4,5)P$_3$ but was without effect on the accumulations of Inositol phosphate$_1$ and Inositol phosphate$_2$. Lower concentrations were ineffective. These data indicate an increase in sensitivity of myocardial tissue to neomycin of more than 10 fold during post-ischaemic reperfusion.

Subsequent experiments were performed to establish whether this inhibitory effect of neomycin was a class effect of aminoglycosides and if so whether other members might have higher potency. Streptomycin and gentamicin were chosen for these studies with a view to using available plasma assays for in vivo studies. As is shown in Table 1, both gentamicin and streptomycin were more potent inhibitors of reperfusion-induced Ins(1,4,5)P$_3$ release than neomycin. Thus, inhibition of reperfusion-induced Ins(1,4,5)P$_3$ release is a class effect of the aminoglycosides.

As shown in Table 1, the polyamine, spermine, also was tested and shown to be inhibitory.

More recent studies have investigated the possible contribution of thrombin to the reperfusion arrhythmias. The studies described above used medium-perfused hearts. However, in vivo myocardial ischaemia and reperfusion are associated with local high concentrations of thrombin associated with the thrombus formation responsible for the occlusion. Recent studies from other laboratories have pointed to a direct pro-arrhythmic effect of the thrombus in vivo. Studies in the inventors' laboratory have shown that thrombin directly stimulates release of Ins(1,4,5)P$_3$ in heart tissue and that this release is inhibited by gentamicin at similar concentrations to those required for inhibition of the noradrenaline response under reperfusion conditions.

In summary, reperfusion of hearts following global ischaemia causes release of Ins(1,4,5)P$_3$ and this can either be effected either by neuronally released noradrenaline or by thrombin. Both of these agents would be expected to be present in the heart under ischaemic conditions in vivo.

EXAMPLE 2

Myocardial Function In Vitro

A) Methods
Reperfusion-induced arrhythmias in in situ perfused rat hearts

A model of in situ perfused rat hearts subjected to 20 minutes coronary artery occlusion to induce ischaemia, followed by reperfusion was used to investigate reperfusion-induced arrhythmias.

Rats (250–300 g) were anaesthetised (pentobarbitone 60 mg/kg, I.P.) and heparinised (200 U/rat I.V.) The thorax was then opened and a metal cannula (ID 1 mm) inserted and tied into the ascending aorta, to commence Langendorff perfusion in situ (31). The interval from opening the chest to commencing heart perfusion was between 50 and 70 seconds. The perfusate was Krebs buffer, with coronary flow controlled by a Ismatac peristaltic pump at a rate of 5 ml/g heart weight/min for the non-ischaemic perfusion. At this flow rate the coronary perfusion pressure was between 32–38 mmHg, measured by pressure transducer (Gould Statham model p23) connected to the sidearm of the perfusion line. Following aortic cancellation, pulmonary vessels were tied off. In some preparations, ventricular pressure was measured by inserting a Millar micro-tip transducer catheter into the left ventricular cavity via the apex. All parameters—coronary perfusion pressure, ventricular pressure, and epicardial ECG, were constantly recorded on a Grass model 7 polygraph. Two hearts were perfused and simultaneously studied.

A silk suture (4.0) was positioned loosely around the left coronary artery 2–3 mm from its origin. Two silk releasing rings were placed around the suture for subsequent release of occlusion. Successful occlusion of the artery, inducing regional ischaemia, was indicated by increases in coronary perfusion pressure of at least 30%. Perfusion pressure was adjusted to non-ischaemic perfusion levels during the ischaemic period.

Drugs were added to the perfusion via a Harvard Model 22 pump. The drug flow was less than 1% of perfusion flow to ensure constant perfusate parameters. Unless mentioned otherwise, the drugs were present 10 minutes before, and during the entire ischaemic and reperfusion periods.

Heart preparations were allowed to stabilise for at least 20 minutes prior to commencing studies. Following 10 minute drug incubation, the left coronary artery was ligated to induce local ischaemia, for a period of 20 minutes. At the end of this ischaemic period, the ligature was released and hearts perfused at pre-ischaemic flow for a period of 5 minutes. Ventricular arrhythmias, occurring during ischaemia or during the first 2 minutes of reperfusion were defined according to the Lambeth Conventions (32).

Statistics

Incidence of arrhythmias was analysed using a $\chi^2$ test, with n≧8 for each group.

B) Results

Effects of aminoglycosides on reperfusion- induced arrhythmias

The initial reperfusion-induced release of the second messenger Ins(1,4,5)P$_3$ occurs at a time point associated with reperfusion-induced arrhythmias. Based on the considerations outlined above, this suggested a possible role for Ins(1,4,5)P$_3$ in the development of arrhythmias. Therefore, reperfusion-induced arrhythmias were quantitated, and the effects of compounds which inhibit the Ins(1,4,5)P$_3$ response under these conditions were investigated.

An ischaemic model of coronary occlusion and subsequent reperfusion in in situ perfused rat hearts was used, and provided a high percentage of ventricular arrhythmias under both ischaemic and reperfused conditions. Twenty minutes regional ischaemia by coronary artery occlusion resulted in 83% (10/12) incidence of VT. As shown in Table 2, reperfusion following this ischaemic period resulted in VT and degenerative VF in 10 out of the 12 rats studied. In all cases, a large number of premature ventricular beats were observed. None of the hearts which became arrhythmic with VT and subsequent VF recovered during the 5 minute reperfusion period studied.

The effects of neomycin on these reperfusion-induced arrhythmias are shown in table 2. Neomycin at 0.05 mM had no significant effect on the induced arrhythmias with 6 out of 8 rats studied showing both severe VT and VF throughout reperfusion. In contrast, and in parallel with [$^3$H]-labelled Inositol phosphate studies, higher concentrations of neomycin (0.5 mM) prevented the occurrence of reperfusion-induced arrhythmias with none of the 10 rats studied exhibiting VT or VF. Similar effects were observed with 5 mM neomycin. The inhibition of reperfusion-induced arrhythmias by 0.5 mM neomycin was independent of any haemodynamic effects as heart rate and ventricular pressure, while dropping upon initial introduction of the drug, recovered to levels not significantly differing from control during the 10 minute incubation period prior to occlusion.

As is shown in Table 1, streptomycin, gentamicin and spermine also inhibited reperfusion arrhythmias in parallel with their effects on reperfusion-induced release of Ins(1,4,5)P$_3$. Gentamicin was the most potent agent tested followed by streptomycin. At the higher concentrations gentamicin and streptomycin also produced a partial inhibition of arrhythmias occurring during the ischaemic phase. These data further suggest the possibility of a contribution by Ins(1,4,5)P$_3$ to these arrhythmias in addition to its apparently essential role in reperfusion arrhythmias.

Thus, inhibition of hydrolysis of phosphatidylinositol(4,5)bisphosphate (PtdIns(4,5)P$_2$) under reperfusion conditions prevents the development of reperfusion arrhythmias.

Effect of staurosporine on reperfusion-induced arrhythmias

In addition to Ins(1,4,5)P$_3$, the second messenger DAG is also produced upon hydrolysis of PtdIns(4,5)P$_2$. DAG activates various isoforms of protein kinase C which in turn controls a number of cellular processes. Thus, it was possible that the anti-arrhythmic effects of the aminoglycosides was be due to inhibition of DAG production and subsequent PKC activation. Therefore, the effects of a potent protein kinase C inhibitor staurosporine (33) on reperfusion-induced arrhythmias was investigated. Staurosporine ($10^{-7}$ M, a concentration known to inhibit PKC in the myocardium under reperfusion conditions (34)) did not significantly alter the percentage incidence of reperfusion-induced arrhythmias from untreated controls as shown in Table 1.

TABLE 1

|  | Ins(1,4,5)P$_3$ | | Reperfusion-induced arrhythmias | | | |
|---|---|---|---|---|---|---|
|  | | | VT | | VF | |
|  | mass | p | % | p | % | p |
| control | 200 ± 18 |  | 83 |  | 83 |  |
| 0.05 mM neomycin | 184 ± 7 | ns | 75 | ns | 70 | ns |
| 0.5 mM neomycin | 121 ± 11 | <.025 | 0 | <.005 | 0 | <.005 |
| 5 mM neomycin | 104 ± 12 | <.025 | 0 | <.005 | 0 | <.005 |
| 0.5 mM spermine | 182 + 4 | ns | 63 | ns | 36 | <.025 |
| 5 mM spermine | 160 ± 9 | <.05 | 30 | <.025 | 20 | <.005 |
| PTX (25 µg/kg) | 128 ± 28 | <.05 | 40 | ns | 10 | <.001 |
| 0.015 mM genta | 145 ± 2 | <0.05 | 58 | <.025 | 25 | <.025 |
| 0.15 mM genta | 136 ± 22 | <0.05 | 27 | <.025 | 27 | <.025 |
| 1.5 mM genta | 102 ± 17 | <0.01 | 17 | <.025 | 8 | <.025 |
| 0.015 mM strep | 201 ± 16 | ns | 45 | ns | 27 | <.025 |
| 0.15 mM strep | 167 ± 5 | <0.05 | 25 | <.025 | 6 | <.025 |
| 1.5 mM strep | 94 ± 11 | <0.01 | 45 | <.025 | 27 | <.025 |
| .1 µM stauro | nd |  | 83 | ns | 69 | ns |

Table 1: Effects of a number of agents on the release of Ins(1,4,5)P$_3$ and reperfusion-induced arrhythmias. Values shown are Ins(1,4,5)P$_3$ content in pmol/mg protein, mean±SEM of data from 4 different hearts 2 minutes after commencing reperfusion following 20 min global ischaemia, and % incidence of ventricular tachycardia (VT) and ventricular fibrillation (VF) in the experimental group (n≧8). Pertussis toxin (PTX) was given by I.P. injection 48 h prior to experimentation. "Genta" is gentamicin, "strep" is streptomycin and "stauro" is staurosporine. Statistical analysis of Ins(1,4,5)P$_3$ mass data was performed using Student's unpaired "t" test and analysis of arrhythmia data using a $\chi^2$ test. p values are relative to control.

Effect of inhibition of phospholipase C β

To date, few direct inhibitors of phosphatidylinositol-specific phospholipase C have been available. However, one compound, a steroid derivative known as U-73122, has been shown to inhibit PLC-β isoforms. As explained above, this agent did not inhibit release of Ins(1,4,5)P$_3$ in intact heart preparations and was without anti-arrhythmic activity. These data are summarised in Table 2.

Taken together, the data derived from a number of different compounds show that inhibition of release of Ins(1,4,5)P$_3$ causes an inhibition of reperfusion arrhythmias.

Arrhythmic effect of thrombin under reperfusion conditions

The finding that thrombin directly stimulated release of Ins(1,4,5)P$_3$ in heart indicates the possibility that thrombin might cause arrhythmias directly via this mechanism. Experiments were performed using hearts from reserpinized rats so that arrhythmic events initiated by noradrenaline were eliminated. Reperfusion arrhythmias were not observed in hearts from reserpinized animals. However, when thrombin (2 U/ml) was added to the perfusate a high incidence of reperfusion arrhythmias was observed. Furthermore, these arrhythmias were inhibited by gentamicin, indicating a relationship to release of Ins(1,4,5)P$_3$ (Table 2).

TABLE 2

Arrhythmic effect of thrombin and its inhibition by gentamicin.

|  | VT% | VF% | n | p |
|---|---|---|---|---|
| reserpine | 44 | 0 | 9 |  |
| thrombin (2 U/ml) | 89 | 67 | 9 | <.05 |
| thrombin + gentamicin | 60 | 0 | 5 | <0.05* |
| control | 100 | 63 | 46 |  |
| U-73122 ($10^{-6}$M) | 88 | 61 | 12 | ns |

*relative to thrombin. Other p values are relative to control.

In summary, agents which stimulate release of Ins((1,4,5)P$_3$ under reperfusion conditions are pro-arrhythmic and agents which inhibit release are anti-arrhythmic.

EXAMPLE 3

In Vivo Studies

A) Methods

Gentamicin was chosen for studies of anti-arrhythmic action of aminoglycoside in vivo because it is the most potent agent in vitro and because an assay method for measuring plasma levels is currently available. Rats were not heparinised so that effects of thrombin will be contributory to observed arrhythmias.

In vivo model for coronary artery occlusion and reperfusion

Rats were anaesthetised with pentobarbitone (60 mg/Kg IP) and artificially ventilated with room air. The chests were opened via the forth intercostal space, and the heart exposed. A 4.0 suture was placed around the left coronary artery and then passed through a guided polyethylene cannula. The thorax was closed leaving the threaded cannula outside the chest. The right carotid artery was cannulated for recording of arterial blood pressure. After stabilisation for 20–30 minutes, the left coronary artery was ligated by pulling the ends of the ligature through the tube and securing them by clamping the tube together with the threads. The ischaemic period was 10 minutes followed by reperfusion. Arterial blood pressure and a lead II ECG was recorded 3 minutes before and during ischaemia, and for the first 5 minutes of reperfusion. In the in vivo rat model, the highest incidence of reperfusion arrhythmias occurs after a 10 minute period of coronary artery occlusion. The size of the ischaemic area was determined at the end of the experiment by the dye method. There was no difference in ischaemic area between hearts from control animals and those receiving gentamicin. Gentamicin was infused at a dose of 2.5–10 mg/Kg/min prior to initiation of ischaemia and maintained throughout the protocol. This caused a moderate reduction in blood pressure and heart rate.

As is shown in Table 3, gentamicin inhibited the development of reperfusion arrhythmias in vivo. The arrhythmias generated under these conditions would be expected to be initiated by noradrenaline and by thrombin and possibly also by other agents. It is important to note that gentamicin was effective also against the arrhythmias occurring under ischaemic conditions. As indicated above, release of Ins(1,4,5)$P_3$ also can occur under these conditions, depending on the severity of the ischaemia.

TABLE 3

|  | VT% | VF% | n | p |
|---|---|---|---|---|
| control | 100 | 68 | 13 |  |
| gentamicin | 30 | 0 | 10 | <0.01 |

Table 3: Effect of gentamicin on reperfusion arrhythmias in vivo.

In summary, gentamicin is a very effective agent in inhibiting reperfusion arrhythmias in vivo.

EXAMPLE 4

Cardiac Selective PLC Inhibitor

Studies from the inventors show that inhibition of release of Ins(1,4,5)$P_3$ under conditions of post-ischaemic reperfusion inhibits the development of reperfusion arrhythmias. This could be achieved either by directly binding to and inhibiting the PLC enzyme which hydrolyses PtdIns(4,5)$P_2$ to Ins(1,4,5)$P_3$ or by binding PtdIns(4,5)$P_2$ and thereby inhibiting PLC activity less directly. Given that the PtdIns turnover pathway occurs in all cell types, it is important to incorporate some selectivity into inhibitory agents if they are to be effective clinical tools. The PLC which is coupled to $\alpha_1$-adrenoceptors in heart provides one possible target for a direct enzyme inhibitor because it is a different enzyme from any of the currently described PLC classes (17). However, agents like the aminoglycosides which bind PtdIns(4,5)$P_2$ can also be appropriate. The inventors have shown that the potency of these compounds increases by more than an order of magnitude under ischaemic conditions. Furthermore, even though the aminoglycosides act by binding PtdIns(4,5)$P_2$, the relative potencies of the aminoglycosides in causing an inhibition of PLC activity differ for the different PLC isoforms and neomycin rather than gentamicin is generally most potent (Table 4). PtdIns(4,5)$P_2$ is an activator rather than a substrate for phosphatidylcholine-specific phospholipase D. For this enzyme, aminoglycosides have been shown to inhibit the activation by PtdIns(4,5)$P_2$ but the rank order of potencies was different from observed in studies of PLC. Thus, even though the aminoglycosides act by binding PtdIns(4,5)$P_2$, this binding clearly affects different enzymes which interact with PtdIns(4,5)$P_2$ differently.

Thus, the development of a suitably selective agent will be possible by either of these mechanisms.

TABLE 4

|  | PC-PLD brain | PI-PLC kidney cy | PI-PLC kidney me | PI-PLC heart rep |
|---|---|---|---|---|
| neomycin | 65 | 30 | 200 | 400 |
| streptomycin | 125 | 380 | 2850 | 150 |
| gentamicin | ND | 130 | 500 | 15 |

Table 4: Relative potencies of neomycin, streptomycin and gentamicin in inhibiting PLC hydrolysing PtdIns(4,5)$P_2$ or in inhibiting the stimulatory effect of PtdIns(4,5)$P_2$ on PLC activity. Values shown are average $EC_{50}$ values×$10^{-6}$ M. Kidney cy and kidney me refer to cytosolic and membrane enzymes, respectively. Heart rep refers to hearts under reperfusion conditions. Brain and kidney data are from the literature (35).

EXAMPLE 5

Anti-Arrhythmic Agents

Currently available anti-arrhythmic agents are only poorly effective and their use is often limited by significant side effects. Furthermore, these agents target primarily the arrhythmias occurring during ischaemia and are essentially ineffective against the arrhythmias which occur following reperfusion (36). Gentamicin in vitro and in vivo is very effective in inhibiting reperfusion arrhythmias. These findings set the stage for the development of an entirely new class of anti-arrhythmic agent based on the inhibition of release of Ins(1,4,5)$P_3$. Furthermore, it is likely that arrhythmias developed in vivo are mechanistically more complex than those observed in in vitro model systems and that Ins(1,4,5)$P_3$ may have a wider role than classical "reperfusion" arrhythmias, as suggested both by our modelling studies and by the in vivo experiments. Conditions such as unstable angina likely involve repeated transient occlusions of the coronary artery and thus repeated episodes of ischaemia and reperfusion. Thus, agents which act by inhibition of release of Ins(1,4,5)$P_3$ may have wider clinical implications than classical "reperfusion" arrhythmias.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

REFERENCES

1. Berridge M J: Cell Signalling—A Tale of 2 Messengers. *Nature*. 1993;365:388–389.

2. Berridge M J: Inositol trisphosphate and diacylglycerol: two interacting second messengers. *Ann Rev Biochem*. 1987;56: 159–193.

3. Irvine R F: Is Inositol Tetrakisphosphate the 2nd Messenger That Controls Ca2+ Entry into Cells. *Adv Second Messenger and Phosphoprotein Res*. 1992;26:161–185.

4. Glennon M C, Shears S B: Turnover of Inositol Pentakisphosphates, Inositol Hexakisphosphate and Diphosphoinositol Polyphosphates in Primary Cultured Hepatocytes. *Biochem J.* 1993;293:583–590.

5. von Harsdorf R, LAng R, Fullerton M, Woodcock E: Myocardial stretch stimulates phosphatidylinositol turnover. *Circ Res.* 1989;65:494–501.

6. Kentish J C, Barsotti R J, Lea T J, Mullican I P, Patel J R, Ferenczi M A: Calcium release from cardiac sarcoplasmic reticulum induced by photorelease of calcium or Ins(1,4,5)$P_3$. *Am J Physiol.* 1990;258:H610–H615.

7. Berridge M: Inositol trisphosphate and calcium signalling. *Nature.* 1993;361:315–325.

8. Zhu Y, Nosek T M: Inositol trisphosphate enhances Ca2+ oscillations but not Ca2+- induced Ca2+ release from cardiac sarcoplasmic reticulum. *Pflugers Arch.* 1991;418:1–6.

9. Gilbert J C, Shirayama T, Pappano A J: Inositol Trisphosphate Promotes Na—Ca Exchange Current by Releasing Calcium from Sarcoplasmic Reticulum in Cardiac Myocytes. *Circ Res.* 1991;69: 1632–1639.

10. Woodcock E A, Smith A I, Wallace C A, White L B S: Evidence for a lack of inositol-(1,4,5)trisphosphate kinase activity in norepinephrine- perfused rat heart. *Biochem Biophys Res Commun.* 1987;148:68–77.

11. Woodcock E, Suss M, Anderson K: Inositol phosphate release and metabolism in rat left atria. *Cirs Res.* 1995;(in press):

12. Heathers G P, Evers A S, Corr P B: Enhanced inositol trisphosphate response to a1-adrenergic stimulation in cardiac myocytes exposed to ischaemia. *J Clin Invest.* 1989;83:1409–1413.

13. Corr P B, Yamada K A, Da Torre S D: Modulation of a-adrenergic receptors and their coupling in ischaemic heart. *Basic Res Cardiol.* 1990;85:31–45.

14. Sharma A, Saffiz J, lee B, Sobel B: Alpha adrenergic-mediated accumulations of calcium in reperfused myocardium. *J Clin Invest.* 1983;72:802–818.

15. Corr P B, Yamada K A, Da Torre S D: Modulation of a-adrenergic receptors and their coupling in ischaemic heart. *Basic Res Cardiol.* 1990;85:31–45.

16. Nakaoka H, Perez D M, Baek K J, Das T, Husain A, Misono K, Im M J, Graham R M: G(h): A GTP-binding protein with transglutaminase activity and receptor signaling function. *Science.* 1994;264:1593–1596.

17. Im M-J, Gray C, Rim A: Characterization of a phospholipase C activity regulated by the purified Dh in reconstitiution systems. *J Biol Chem.* 1992;267:8887–8894.

18. Bleasdale J, Thakur N, Gremban R, Bundy G, Fitzpatrick F, Smith R, Bunting S: Selective inhibition of receptor-coupled phospholipase C-dependent processes in human platelets and polymorphonuclear neutrophils. *J Pharmacol Exp Ther.* 1990;256:756–768.

19. Sheridan D J: Alpha adrenoceptors and arrhythmias. *J Mol Cell Cardiol.* 1986; 18:59–68.

20. Shears S B: Metabolism of Inositol Phosphates. *Adv Second Messenger and Phosphoprotein Res.* 1992;26:63–92.

21. Anderson K, Dart A, Woodcock E: Inositol phopshate release and metabolism during myocardial ischemia and reperfusion in rta heart. *Circ Res.* 1995;(in press):

22. Woodcock E, Tanner J: The preparation of samples for high performance liquid chromatography of inositol phosphates. *J Chromatography—Biomed Appl.* 1992;134–138.

23. Woodcock E, Anderson K, Land S: Lyophilization can generate artifacts in chromatographic profiles of inositol phosphates. *J Chromatogr.* 1993;619:121–126.

24. Woodcock E, Anderson K: Inositol phosphates in rat atria and the importance of the extraction procedure. *J Mol Cell Cardiol.* 1993;25:215–227.

25. Eisenhofer G, Goldstein D, Stull R, Keiser H, Sunderland T, Murphy D, Kopin I: Simultaneous liquid-chromatographic determination of 3,4-dihydrophenolglycol, catecholamines and 3,4-dihydroxyphenylalanine in plasma, and their responses to inhibition of monoamine oxidase. *Clin Chem.* 1986;32:2030–2033.

26. Divecha N, Banfic H, Irvine R F: The Polyphosphoinositide Cycle Exists in the Nuclei of Swiss 3T3 Cells Under the Control of a Receptor (for IGF-I) in the Plasma Membrane, and Stimulation of the Cycle Increases Nuclear Diacylglycerol and Apparently Induces Translocation of Protein Kinase-C to the Nucleus. *EMBO J.* 1991;10:3207–3214.

27. Bird G S, Burgess G M, Putney J W: Sulfhydryl Reagents and cAMP-Dependent Kinase Increase the Sensitivity of the Inositol 1,4,5-Trisphosphate Receptor in Hepatocytes. *J Biol Chem.* 1993;268:17917–17923.

28. Schomig A, Dart A, Dietz R, Mayer E, Kubler W: Release of endogenous catecholamines in the ischemic myocardium of the rat. Part A: Locally mediated release. *Circ Res.* 1984;55:689–701.

29. Gabev E, Kasianowicz J, Abbott T, McLauchlin S: Binding of neomycin to phosphatidylinositol 4,5-bisphosphate. *Biochem Biophys Acta.* 1989;979:105–122.

30. Tysnes O B, Verhoeven A J M, Holmsen H: Neomycin inhibits agonist-stimulated polyphosphoinositide metabolism and responses in human platelets. *Biochem Biophys Res Commun.* 1987;144:454–462.

31. Du X, Dart A, Riemersma R, Oliver M: Sex differences in presynaptic adrenergic inhibition of noradrenaline release during normoxia and ischemia in the rat heart. *Circ Res.* 1991;68:827–835.

32. Walker M, Curtis M, Hearse D, et al.: The Lambeth Conventions: guidelines for the study of arrhythmias in ischaemia, infarction, and reperfusion. *Cardiovasc Res.* 1988;22:447–455.

33. Tamaoki T, Nomoto H, Takahashi I, Kato Y, Morimoto M, Tomita F: Staurosporine, a potent inhibitor of phospholipib/Ca2+ dependent protein kinase. *Biochem Biophys Res Commun.* 1986;135:397–402.

34. Strasser R H, Braun-Dullaeus R, Walendzik H, Marquetant R: a1-receptor-independent activation of protein kinase C in acute myocardial ischemia. Mechanism for sensitization of the adenylyl cyclase system. *Circ Res.* 1992;70:1304–1312.

35. Liscovitch M, Chalifa V, Danin M, Eli Y: Inhibition of neural phospholipase D activity by aminoglycoside antibiotics. *Biochem J.* 1991;279:319–321.

36. Heidbuchel H, Tack J, Vanneste L, Ballet A, Ector H, Werf F Vd: Significance of arrhythmias during the first 24 hours of acute myocardial infarction treated with alteplase and effect of early administration of a β-blocker or a bradycardiac agent on their incidence. *Circulation.* 1994;89:1051–1059.

We claim:

1. A method for the prophylaxis or treatment of cardiac arrhythmia in a mammal said method comprising administering to said mammal an effective amount of an agent capable of blocking formation or release of inositol (1,4,5) triphosphate (Ins(1,4,5)$P_3$) in cardiac tissue.

2. A method according to claim 1 wherein the cardiac arrhythmia comprises tachycardia and fibrillations of cardiac sites.

3. A method according to claim 1 wherein the agent inhibits or prevents release of $Ins(1,4,5)P_3$ from phospholipid $PtdIns(4,5)P_2$.

4. A method according to claim 3 wherein the agent is an aminoglycoside.

5. A method according to claim 4 wherein the aminoglyoside is selected from the list consisting of gentamicin, tobramycin, amikacin, netilimicin, kanamycin, streptomycin and neomycin or derivatives thereof.

6. A method according to claim 3 wherein the agent is a polyamine.

7. A method according to claim 6 wherein the polyamine is spermine or a derivative thereof.

8. A method according to claim 1 wherein the agent blocks the effects of $Ins(1,4,5)P_3$.

9. A method according to claim 8 wherein the agent blocks the $Ins(1,4,5)P_3$ receptor.

10. A method according to claim 8 wherein the agent is an antagonist of $Ins(1,4,5)P_3$.

11. A method according to claim 1 wherein the agent is administered by oral, parenteral or buccal administration.

12. A method according to claim 1 wherein the effective amount is from about 0.1 to about 100 mg per kilogram of body weight of the mammal.

13. A method according to claim 12 wherein the effective amount is from about 5 to about 60 mg per kilogram of body weight of the mammal.

14. A method according to claim 1 further comprising the sequential or simultaneous administration of an additional anti-arrhythmia drug.

15. A method according to claim 14 wherein the additional anti-arrhythmia drug is selected from the list consisting of amiodorone, sotalol and lignocaine.

16. A method according to claim 1 further comprising the sequential or simultaneous administration of an agent capable of effecting thrombolysis.

17. A method according to claim 16 wherein the agent capable of effecting thrombolysis selected from the list consisting of streptokinase, urokinase and tissue plasminogen activator.

18. A method according to claim 1 further comprising the sequential or simultaneous administration of an agent which increases cardiac systolic and/or diastolic function.

19. A method according to claim 18 wherein said agent which increases cardiac function is selected from the list consisting of dioxin, dobutamine, nitrates, captopril, nifedipine and frusemide.

20. A method according to claim 1 wherein the mammal is a human.

21. A pharmaceutical composition comprising an agent capable of blocking formation or release of $Ins(1,4,5)P_3$ in cardiac tissue and further comprising another anti-arrhythmia drug and a pharmaceutically acceptable carrier or diluent.

22. A pharmaceutical composition comprising an agent capable of blocking formation or release of $Ins(1,4,5)P_3$ in cardiac tissue and further comprising an agent capable of effecting thrombolysis and a pharmaceutically acceptable carrier or diluent.

23. A pharmaceutical composition comprising an agent capable of blocking formation or release of $Ins(1,4,5)P_3$ in cardiac tissue and further comprising an agent which increases cardiac systolic and/or diastolic function and a pharmaceutically acceptable carrier or diluent.

24. A pharmaceutical composition according to claim 21 or 22 or 23 wherein said agent inhibits or prevents release of $Ins(1,4,5)P_3$ from phospholipid $PtdIns(4,5)P_2$.

25. A pharmaceutical composition according to claim 24 wherein said agent is an aminoglycoside.

26. A pharmaceutical composition according to claim 25 wherein said agent is selected from the list consisting of gentamicin, tobramycin, amikacin, netilimicin, kanamycin, streptomycin and neomycin or derivatives thereof.

27. A pharmaceutical composition according to claim 24 wherein said agent is a polyamine.

28. A pharmaceutical composition according to claim 27 wherein said agent is spermine or a derivative thereof.

29. A pharmaceutical composition according to claim 21 wherein said other anti-arrhythmia drug is selected from the list consisting of amiodorone, sotalol and lignocaine.

30. A pharmaceutical composition according to claim 22 wherein the agent capable of effecting thrombolysis is selected from the list consisting of streptokinase, urokinase and tissue plasminogen activator.

31. A pharmaceutical composition according to claim 23 wherein said agent which increases cardiac function is selected from the list consisting of dioxin, dobutamine, nitrates, captopril, nifedipine and frusemide.

* * * * *

UNITED STATES PATENT AND TRADEMARK OFFICE
CERTIFICATE OF CORRECTION

PATENT NO. : 5,929,039

DATED : July 27, 1999

INVENTOR(S) : Woodcock et al.

It is certified that error appears in the above-identified patent and that said Letters Patent is hereby corrected as shown below:

Title page, Column 2, [56] References Cited, FOREIGN PATENT DOCUMENTS: "WO900061" should read -- WO9000061 --;

Title page, Column 2, [56] References Cited, OTHER PUBLICATIONS: Under Casti et al., "16179n" should read -- 161791n --;

Column 5, line 63, "37°" should read -- 37° --;

Column 16, line 64, "mammal said" should read -- mammal in need thereof said --;

Column 17, line 41, "selected" should read --is selected--.

Signed and Sealed this

Twenty-sixth Day of December, 2000

Attest:

Q. TODD DICKINSON

*Attesting Officer*  *Director of Patents and Trademarks*